United States Patent
Regan et al.

(10) Patent No.: US 11,085,070 B2
(45) Date of Patent: *Aug. 10, 2021

(54) AMPLIFICATION REPORTER WITH BASE-PAIRING OLIGOMERS

(71) Applicant: Bio-Rad Laboratories, Inc., Hercules, CA (US)

(72) Inventors: John F. Regan, San Mateo, CA (US); Dianna Maar, Mountain House, CA (US); Dawne N. Shelton, San Ramon, CA (US); Tina C. Legler, Tracy, CA (US); Samantha Cooper, Berkeley, CA (US); Wei Yang, Dublin, CA (US); Eli A. Hefner, Fairfield, CA (US); Niels Klitgord, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/834,854

(22) Filed: Mar. 30, 2020

(65) Prior Publication Data

US 2020/0270677 A1 Aug. 27, 2020

Related U.S. Application Data

(63) Continuation of application No. 15/411,482, filed on Jan. 20, 2017, now Pat. No. 10,604,789, which is a
(Continued)

(51) Int. Cl.
*C12Q 1/68* (2018.01)
*C12Q 1/6818* (2018.01)
(Continued)

(52) U.S. Cl.
CPC ......... *C12Q 1/6818* (2013.01); *C12Q 1/6823* (2013.01); *C12Q 1/6848* (2013.01)

(58) Field of Classification Search
None
See application file for complete search history.

(56) References Cited

U.S. PATENT DOCUMENTS

2004/0053254 A1\* 3/2004 Wangh .................. C07H 21/00
435/6.1

OTHER PUBLICATIONS

Kong et al. (Duplex probes: a new approach for the detection of specific nucleic acids in homogenous assays, Analytics Chimica Acta, vol. 491, Issue 2, Sep. 8, 2003, pp. 135-143).*
(Continued)

*Primary Examiner* — Aaron A Priest
(74) *Attorney, Agent, or Firm* — Kolisch Hartwell, P.C.

(57) ABSTRACT

System, including methods, apparatus, and compositions, for performing amplification assays with an amplification reporter including a first oligomer and a second oligomer capable of base-pairing with one another below a melting temperature of the reporter. The reporter may have a detectable photoluminescence that is affected, such as reduced, by base-pairing of the first and second oligomers with one another. A target, such as a nucleic acid target sequence, may be amplified in at least one volume, such as a plurality of partitions, above the melting temperature, and photoluminescence of the reporter may be detected from the at least one volume below the melting temperature. A property of the target, such as a concentration of the target, may be determined based on the photoluminescence detected.

9 Claims, 24 Drawing Sheets

Specification includes a Sequence Listing.

Related U.S. Application Data continuation of application No. 14/457,863, filed on Aug. 12, 2014, now Pat. No. 9,556,475.

(60) Provisional application No. 61/864,788, filed on Aug. 12, 2013.

(51) Int. Cl.
*C12Q 1/6823* (2018.01)
*C12Q 1/6848* (2018.01)

(56) References Cited

OTHER PUBLICATIONS

Sanchez et al. (Two-temperature LATE-PCR endpoint genotyping, BMC Biotechnol. Dec. 4, 2006;6:44).*
Sanchez et al., Linear-after-the-exponential (LATE)-PCR: an advanced method of asymmetric PCR and its uses in quantitative real-time analysis, Proc Natl Acad Sci U S A. Feb. 17, 2004;101(7):1933-8. Epub Feb. 9, 2004.*

* cited by examiner

FLUORESCENCE

LOW

INTERMEDIATE

HIGH

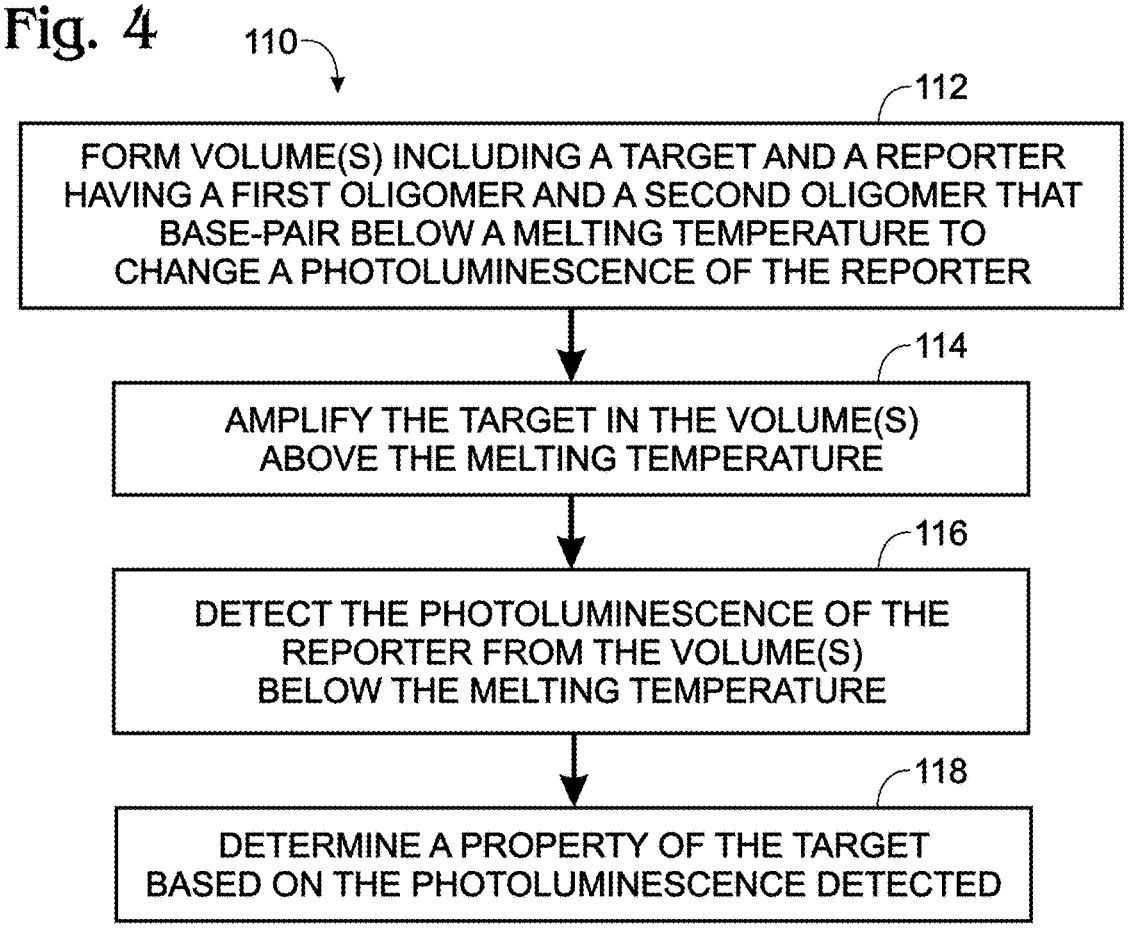
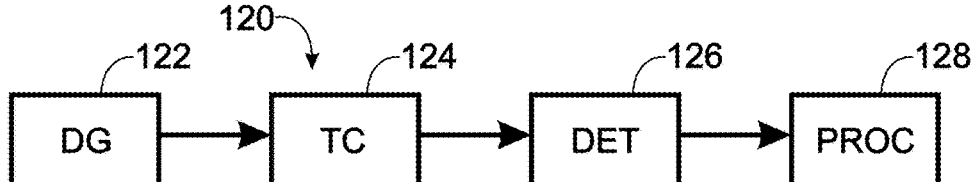
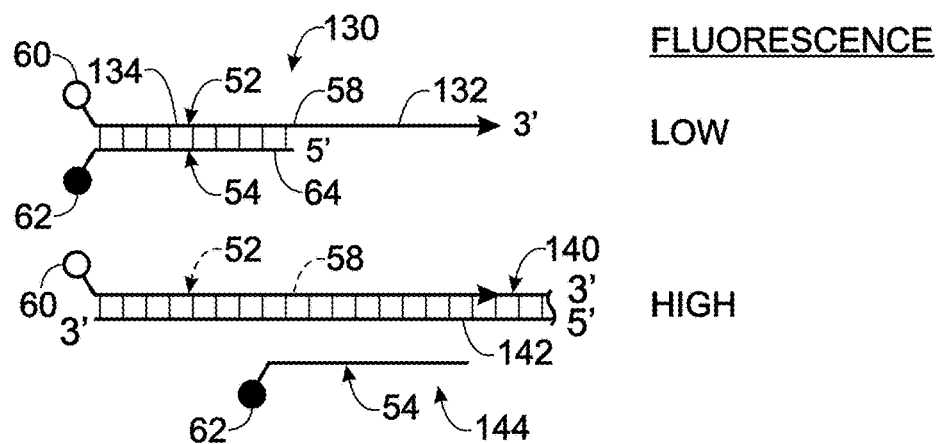

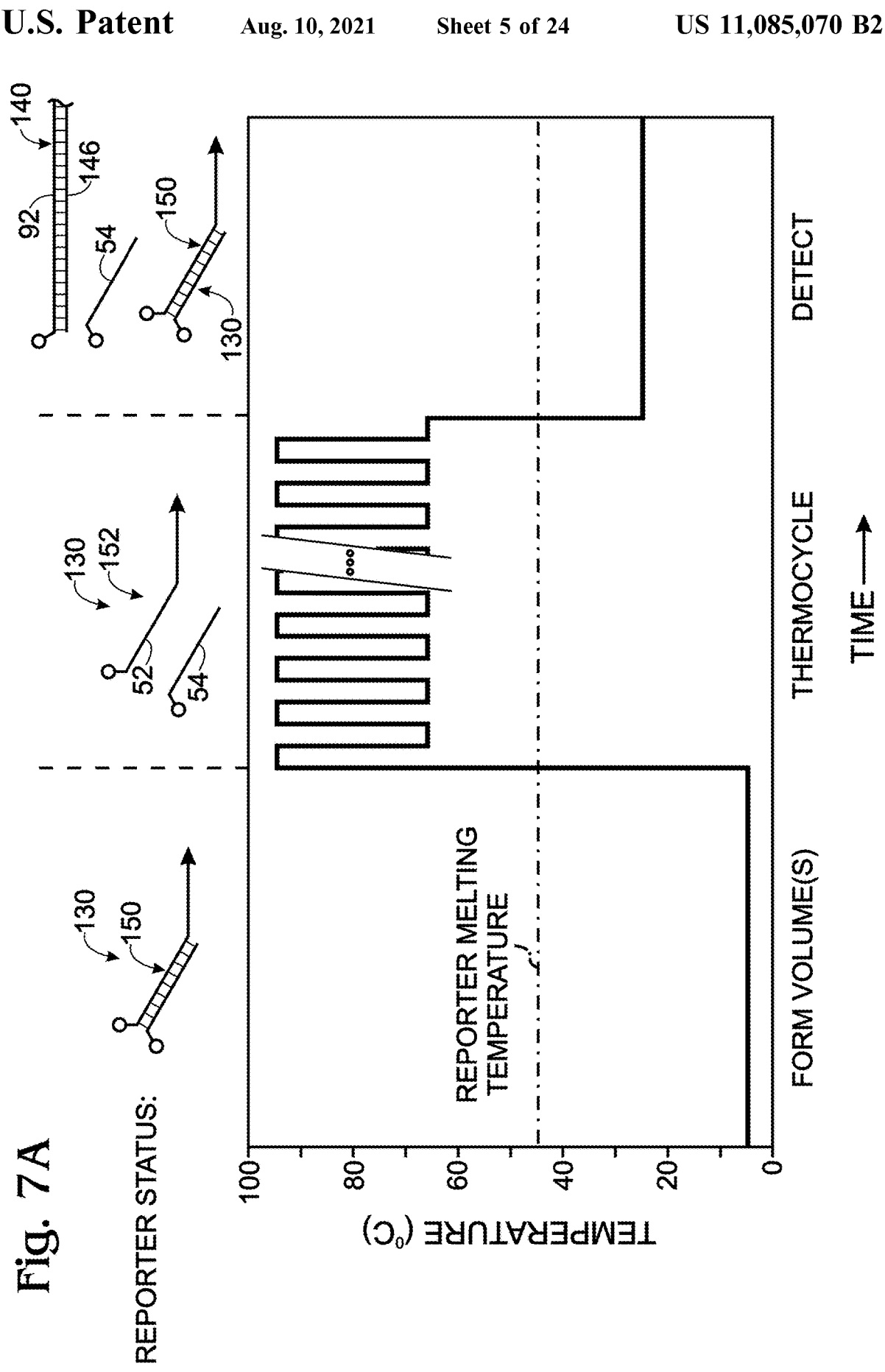

FLUORESCENCE

LOW

HIGH

FLUORESCENCE

LOW

HIGH

Fig. 25
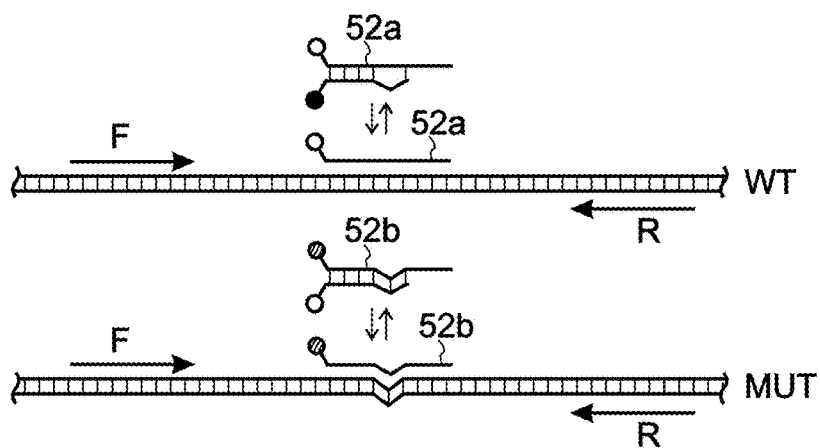
Fig. 26
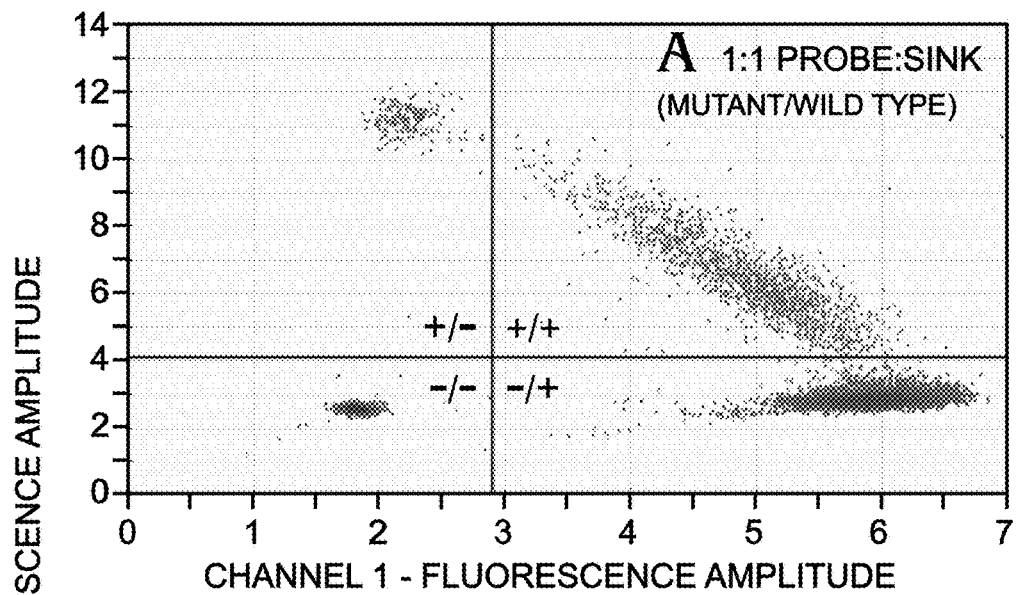
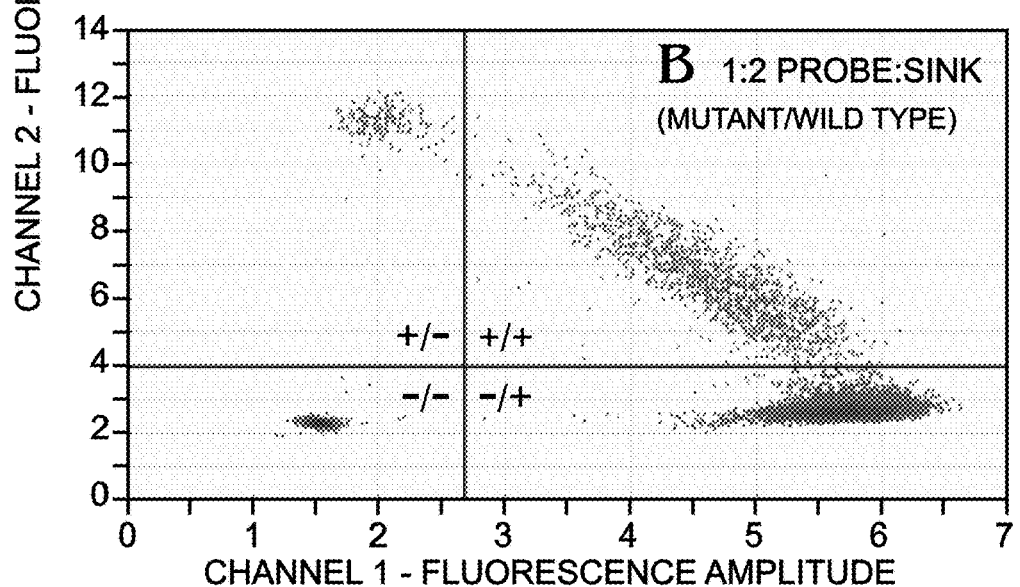

AMPLIFICATION REPORTER WITH BASE-PAIRING OLIGOMERS

CROSS-REFERENCES TO PRIORITY APPLICATIONS

This application is a continuation of U.S. patent application Ser. No. 15/411,482, filed Jan. 20, 2017, now U.S. Pat. No. 10,604,789, which, in turn, is a continuation of U.S. patent application Ser. No. 14/457,863, filed Aug. 12, 2014, now U.S. Pat. No. 9,556,475, which, in turn, is based upon and claims the benefit under 35 U.S.C. § 119(e) of U.S. Provisional Patent Application Ser. No. 61/864,788, filed Aug. 12, 2013. Each of these priority patent applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. Patent Application Publication No. 2012/0194805 A1, published Aug. 2, 2012; U.S. patent application Ser. No. 14/171,754, filed Feb. 3, 2014; and Joseph R. Lakowicz, PRINCIPLES OF FLUORESCENCE SPECTROSCOPY ($2^{nd}$ Ed. 1999).

INTRODUCTION

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, may be described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or, equivalently, the negative fraction then may be utilized to determine the concentration of the analyte in the partitions by Poisson statistics.

Digital assays frequently rely on amplification of a nucleic acid target in partitions to enable detection of a single copy of an analyte. Amplification of the target may be conducted via the polymerase chain reaction (PCR), to achieve a digital PCR assay. Amplification of the target can be detected optically from a probe included in the reaction. The probe may include an oligonucleotide conjugated to a fluorophore and a quencher. The oligonucleotide may be cut as the target is amplified, to separate the fluorophore from the quencher. As a result, light emission from the fluorophore may be quenched more efficiently by the quencher in the absence of target amplification (a negative partition) than in the presence of target amplification (a positive partition). However, the difference in fluorescence between negative partitions and positive partitions can vary with the assay configuration, often diminishing the ability to reliably distinguish the two types of partitions.

A simple and cost-effective approach is needed to minimize noise in probe-based amplification assays, such as in digital PCR assays.

SUMMARY

The present disclosure provides a system, including methods, apparatus, and compositions, for performing amplification assays with an amplification reporter including a first oligomer and a second oligomer capable of base-pairing with one another below a melting temperature of the reporter. The reporter may have a detectable photoluminescence that is affected, such as reduced, by base-pairing of the first and second oligomers with one another. A target, such as a nucleic acid target sequence, may be amplified in at least one volume, such as a plurality of partitions, above the melting temperature, and photoluminescence of the reporter may be detected from the at least one volume below the melting temperature. A property of the target, such as a concentration of the target, may be determined based on the photoluminescence detected.

BRIEF DESCRIPTION OF THE DRAWINGS

FIG. 4 is a schematic flowchart of an exemplary assay performed with a reporter composed of base-pairing oligomers, in accordance with aspects of the present disclosure.

FIG. 5 is a schematic diagram of an exemplary system for performing the assay of FIG. 4, in accordance with aspects of the present disclosure.

FIG. 6 is a schematic comparing levels of fluorescence from (a) an exemplary reporter including a sink base-paired with a probe, with the probe configured as a photoluminophore-labeled primer, and (b) the probe incorporated by primer extension into an amplicon that excludes the sink from base-pairing interaction with the probe, in accordance with aspects of the present disclosure.

FIG. 7A is a graph showing an exemplary thermal profile for stages of the assay of FIGS. 6 and 7, and an exemplary status of the reporter during at least a portion of each stage, in accordance with aspects of the present disclosure.

FIG. 25 is a schematic of another strategy for performing a multiplex assay of wild-type and mutant alleles of a K-Ras gene in droplets, with probes, amplification primers, and a sink aligned with their respective binding sites in wild-type (WT) and mutant (MUT) templates, in accordance with aspects of the present disclosure.

FIG. 26 is a series of scatter plots of fluorescence data collected from a multiplex assay of a K-Ras target performed in droplets according to the strategy of FIG. 25, with two different amounts of the sink present in the droplets, in accordance with aspects of the present disclosure.

FIG. 30A shows results from a "positive" sample containing target DNA. FIG. 30B shows results from a "negative" or no-target sample.

DETAILED DESCRIPTION

Figure 1:
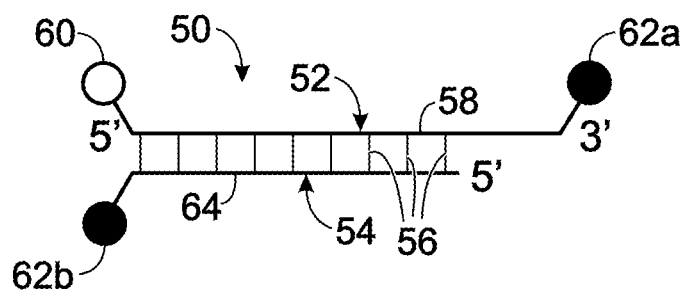
FIG. 1 is a schematic view of an exemplary reporter composed of base-pairing oligomers (a "probe" and a "sink") that collectively provide a photoluminophore and an energy transfer partner, such as a quencher, for the photoluminophore, in accordance with aspects of the present disclosure.

The present disclosure provides a system, including methods, apparatus, and compositions, for performing amplification assays with an amplification reporter including a first oligomer and a second oligomer capable of base-pairing with one another below a melting temperature of the reporter. The reporter may have a detectable photoluminescence that is affected, such as reduced, by base-pairing of the first and second oligomers with one another. A target, such as a nucleic acid target sequence, may be amplified in at least one volume, such as a plurality of partitions, above the melting temperature, and photoluminescence of the reporter may be detected from the at least one volume below the melting temperature. A property of the target, such as a concentration of the target, may be determined based on the photoluminescence detected.

The present disclosure enables lowering the photoluminescent background of partitions that do not contain the product of interest (negative partitions), to increase the difference in magnitude of the signals for negative and positive partitions. A reporter composed of a pair of base-pairing oligomers may be included in the partitions. The reporter may include an energy donor and an energy acceptor that form a proximity-dependent energy transfer pair. The energy donor may be included in one of the oligomers and the energy acceptor in the other, or both may be included in the same oligomer. One of the oligomers, a first (or second) oligomer, may be a "probe" that emits light to be detected. The other of the oligomers, a second (or first) oligomer, may be described as a "sink." The sink affects (e.g., decreases, increases, and/or spectrally shifts, among others) a photoluminescence detectable from the probe/reporter when the probe and the sink are base-paired with one another, relative to when the probe is not base-paired with the sink. For example, the probe may include a photoluminophore that acts as an energy donor, and the sink may include a quencher that acts as an energy acceptor for the photoluminophore, to reduce the basal photoluminescence of the probe in the partitions.

The sink may include an oligonucleotide that is at least partially or fully complementary to the probe, allowing the sink to bind to the probe. The oligonucleotide may, for example, bind to the probe to promote intramolecular and/or intermolecular quenching of the photoluminophore by the quencher. In some examples, the probe may or may not include a quencher, and the sink may include a quencher that reduces photoluminescence emission by the photoluminophore when the sink binds the probe. In any event, a quencher of the probe and/or the sink may, in some cases, quench the photoluminophore of the probe by contact quenching (interchangeably termed static quenching).

In some embodiments, the sink may be configured to bind the probe during only a portion of an assay, based on the thermal profile of the assay. The sink may bind an intact form of the probe at a lower, detection temperature but not substantially at one or more higher, amplification temperatures. The detection temperature (also termed a reading temperature) may be less than about 50, 45, 40, 35, or 30 degrees Celsius, or no more than about room temperature (about 20-25 degrees Celsius)), among others. The sink may not bind substantially to the probe at one or more (or each) amplification temperatures (e.g., an annealing temperature and/or an extension temperature) and/or may not bind substantially to the probe at a minimum temperature used for amplification/thermocycling. Accordingly, the sink may increase quenching of the photoluminophore during detection, without interfering substantially with amplification, thus lowering the detected photoluminescence amplitude of negative partitions. The sink can be easy to design and can be added conveniently to an assay mixture. In other examples, the sink may be configured to bind to a probe during and/or after each amplification cycle, to permit a kinetic analysis of amplification (e.g., a real-time assay) in at least one fluid volume.

The present disclosure may provide a method to differentiate between a successful PCR reaction and an unsuccessful PCR reaction by detecting light at a reading temperature. A probe and a complementary oligomer (a sink) may be mixed with amplification reagents before thermal cycling. The sink may affect the photoluminescence of the probe at the reading temperature, but may not affect the photoluminescence of the probe during thermal cycling, whether or not amplification occurs. The sink may have a melting temperature for base-pairing with the probe that is below standard thermal-cycling conditions, but greater than the reading temperature. The probe and the sink may interact at the reading temperature to provide quenching in the absence of amplification. In the presence of amplification, the sink may interact less with the probe due to competition with an amplicon for binding to the probe, not due to displacement of the sink from the probe during amplification.

Further aspects of the present disclosure are presented in the following sections: (I) overview of reporters composed of base-pairing oligomers, (II) assays, (III) compositions, and (IV) examples.

I. OVERVIEW OF REPORTERS COMPOSED OF BASE-PAIRING OLIGOMERS

Figure 2:
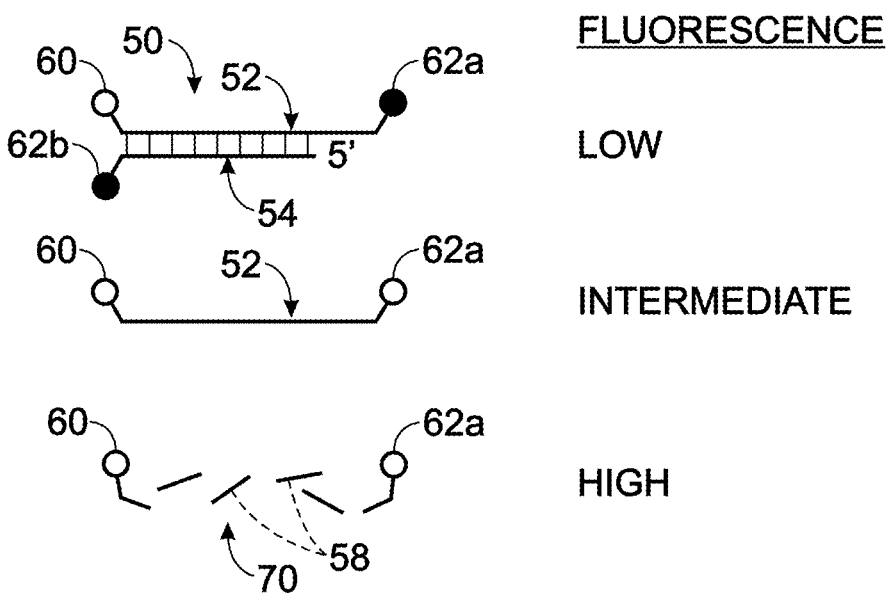
FIG. 2 is a schematic comparing the levels of fluorescence produced by the reporter of FIG. 1 while in a base-paired form, the probe of the reporter of FIG. 1 separated from the sink, and a degraded (cleaved) form of the probe resulting from target amplification, in accordance with aspects of the present disclosure.
Figure 3:
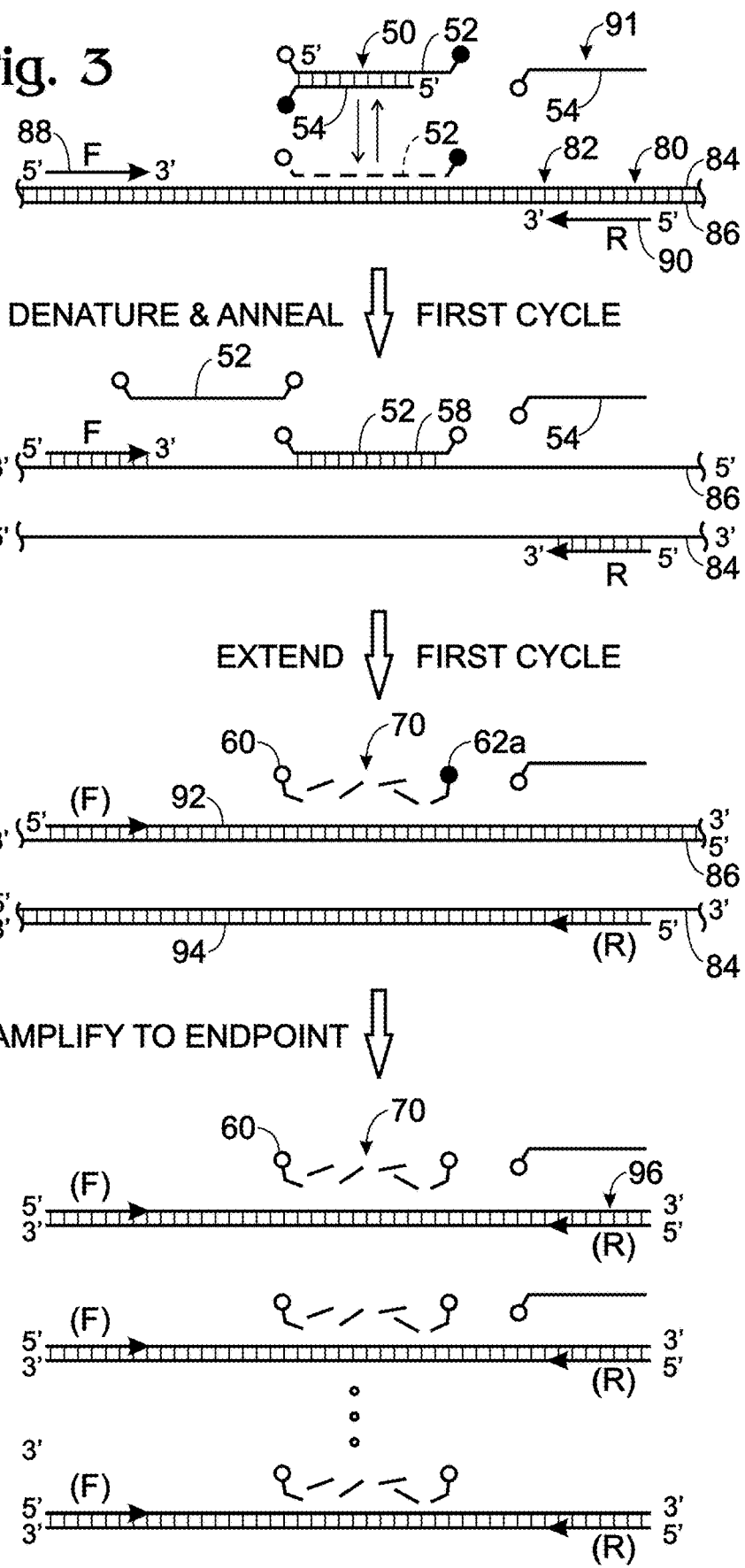
FIG. 3 is a schematic flowchart illustrating selected steps and configurations of an exemplary assay performed with the reporter of FIG. 1, in accordance with aspects of the present disclosure.

This section provides an overview of reporters composed of base-pairing oligomers and illustrates use of an exemplary reporter in an amplification assay to lower the background signal; see FIGS. 1-3.

FIG. 1 shows an exemplary reporter 50 having a base-paired configuration formed by binding of a probe 52 to a sink 54 via a series of base pairs 56. The base pairs are intended to be schematic and may not (or may) represent the actual number of base pairs formed, here or elsewhere in the present disclosure. The reporter interchangeably may be described as a reporter system and may have the base-paired form shown in FIG. 1, and at least one separated form. A separated form can be created by melting (also termed denaturing) the base-paired form. Other separated forms can be created, at least in part, by modifying the probe and/or the sink, such as by extension or degradation.

The probe and the sink each may be a different oligomer. The oligomer may have a body formed by a chain (e.g., an oligonucleotide) of conjugated units, such as nucleotides or nucleotide analogues, each containing a base (e.g., a nucleobase). The body of each oligomer may be attached to at least one energy donor and/or at least one energy acceptor of an energy transfer pair, as described below.

Probe 52 may include a body formed by an oligonucleotide 58 (or an oligonucleotide analogue), at least one energy donor, such as a photoluminophore 60, and, optionally, at least one energy acceptor, such as a quencher (e.g., quencher 62*a*). (In some examples, the quencher may be omitted from the probe (e.g., see Section IV).) The photoluminophore and the quencher each may be connected (e.g., conjugated, interchangeably termed covalently linked) to oligonucleotide 58 at any suitable position along the oligonucleotide, such as at respective opposite ends of the oligonucleotide from each other. For example, in the depicted embodiment, photoluminophore 60 is attached to the 5'-end and quencher 62*a* is attached to the 3'-end of oligonucleotide 58. In other cases, at least one quencher may be positioned internally, between the 5'- and 3'-ends of the oligonucleotide (e.g., as in a ZEN™ probe from Integrated DNA Technologies).

Probe 52 may or may not act as a primer for target amplification. If the probe acts as a primer, the probe may be configured to be extended during amplification through the action of a polymerase (and/or ligase), and may define one of the ends of an amplicon resulting from target amplification. For example, the probe may be a forward primer or a reverse primer of a pair of primers for target amplification. (The terms "forward" and "reverse" for primers are arbitrary, interchangeable designations, unless specified otherwise.) If the probe is not intended to act as a primer, the probe may be modified to block its elongation and/or may have one or more mismatches with the template at or near its 3'-end, to discourage extension by polymerase (or ligase). Accordingly, the probe may bind to the end of a target/amplicon, or may bind at a position that is intermediate the binding sites for a forward primer and a reverse primer used for target amplification.

Photoluminophore 60 may be any moiety capable of emitting light (photoluminescing) in response to irradiation with excitation light. Exemplary forms of photoluminescence include fluorescence and phosphorescence, among others. Accordingly, the photoluminophore may, for example, be a fluorophore or a phosphor. Suitable photoluminophores may include a dye, such as a FAM, VIC, HEX, ROX, TAMRA, or JOE dye, or the like. In some examples, the photoluminophore may be replaced with a luminophore capable of chemiluminescence or any other form of luminescence.

Sink 54 may include a body formed by a sink oligonucleotide 64 (or an oligonucleotide analogue) that is at least substantially complementary to probe oligonucleotide 58 and binds specifically to probe 52, at least in part via base pairs 56. The sink may (or may not) include at least one energy donor and/or at least one energy acceptor that form an energy transfer pair with one another. For example, the sink may include at least one quencher (e.g., quencher 62*b*) connected (e.g., conjugated) to sink oligonucleotide 64 at any suitable position along the oligonucleotide. Each donor/acceptor of sink 54 may be connected at a 3'-end of oligonucleotide 64, as shown, at a 5'-end, or intermediate the 3'- and 5'-ends. Quencher 62*b* may be positioned very close to photoluminophore 60 in reporter 50, such as to permit contact quenching. For example, quencher 62*b* and photoluminophore 60 may be conjugated to respective nucleotides that base-pair with one another (i.e., the nucleotides are aligned with one another), or that are offset by no more than two nucleotides or no more than one nucleotide along the base-paired reporter.

Each of oligonucleotides 58 and 64 may have any suitable properties. The oligonucleotide may have any suitable length, such as at least 6, 8, 10, 15, or 20 nucleotides, and/or less than about 200, 100, or 50 nucleotides, among others. The oligonucleotide may be a conventional oligonucleotide or an analogue or derivative thereof. Exemplary analogues/derivatives include peptide nucleic acids, locked nucleic acids, phosphorothiates, etc. Oligonucleotides 58 and 64 may have the same length or different lengths. If the oligonucleotides have different lengths, oligonucleotide 64 may be shorter (or longer) than oligonucleotide 58. In some cases, a reporter with sink oligonucleotide 64 shorter than probe oligonucleotide 58 may be preferable, because the probe then can be designed to bind to the target/amplicon, but not the sink, at the annealing/extension temperature(s) used for amplification. Also or alternatively, the probe may be configured to bind to the template/amplicon with a higher melting temperature than binding to the sink. The oligonucleotides may be configured to form any suitable number of base pairs with one another, such as at least 5, 10, or 15 among others. A base-paired form of the reporter resulting from base pairing of the oligonucleotides with one another may have a melting temperature, in the assay, that is less than the average, maximum, or minimum temperature used for amplification (e.g., less than the annealing/extension temperature(s) used for thermocycling), such as less than about 70, 60, or 50 degrees, among others. In some cases, the probe may be unquenched at the temperatures used for amplification, such that all of the partitions appear to be positive for amplification if photoluminescence is detected from the partitions at an amplification temperature. Oligonucleotide 64 (and sink 54) may be configured to be non-extendable (or extendable) and non-cleavable (or cleavable) by polymerase during amplification. For example, 3' phosphorylation or another modification can be used to prevent the probe (and/or sink) from being extended by polymerase (or ligase) during amplification.

Quenchers 62*a* and 62*b*, interchangeably termed quencher moieties, may have any suitable properties. Each quencher may be configured to reduce an ability of photoluminophore 60 to emit light when excited (e.g., when irradiated with suitable excitation light). If more than one quencher is present in a reporter, a probe, and/or a sink, the quenchers may be copies of one another or may be structurally distinct. A quencher may be a non-photoluminescent or "dark quencher" that is capable of quenching emission of light from the photoluminophore without substantially emitting light itself, or may be a photoluminescent quencher that emits light as a result of energy transfer (e.g., fluorescence resonance energy transfer) from the photoluminophore. Exemplary quenchers that may be suitable include Black Hole® quenchers (BHQ), Iowa Black® dark quenchers (IB), TAMRA dye, and/or the like.

FIG. 2 shows a schematic comparing the levels of fluorescence that may be produced in an assay by a base-paired form of reporter 50, probe 52 separate from sink 54, and a cut form 70 of probe 52 (interchangeably termed a degraded or cleaved probe/reporter). Cut probe 70 may, for example, be formed by amplification of a target, through probe cleavage catalyzed by a polymerase (e.g., Taq DNA polymerase). The lowest level of fluorescence in the schematic is produced by reporter 50, because photoluminophore 60 is quenched by quencher 62a of the probe and/or quencher 62b of sink 54. If sink 54 is omitted from the assay, the level of fluorescence from intact probe 52 is higher than in the presence of the sink. Accordingly, the background level of fluorescence is higher. The highest level of fluorescence is produced by degraded probe 70 because photoluminophore 60 is no longer connected to probe quencher 62a (and/or proximate sink quencher 62b). More particularly, because probe oligonucleotide 58 is degraded, photoluminophore 60 and quencher 62a are no longer covalently linked to one another, and sink 54, if present in the assay, cannot bind stably to the degraded probe.

FIG. 3 shows a schematic flowchart illustrating selected steps and configurations of an exemplary assay performed in partitions with reporter 50 (i.e., probe 52 and sink 54). The configurations shown here may be produced in a partition that contains at least one copy of a template 80 containing a target 82. The template may be double-stranded, with strands 84 and 86, as shown, or single-stranded. A forward primer 88 ("F"), a reverse primer 90 ("R"), and probe 52 are shown at the top of FIG. 3, aligned with corresponding regions of template 80/target 82 at which each can bind (after the template/target is denatured). A second, unbound copy of probe 52 is shown as dashed because sink 54 may be in molar excess relative to the probe, indicated by an unbound copy of the sink at 91, such that substantially all of the probe is bound to the sink at room temperature, before amplification has begun.

A first cycle of target amplification may be initiated by heating template 80 above its denaturation temperature. Annealing then may be performed at a lower temperature that permits the forward primer and probe 52, and the reverse primer, to bind specifically to single strands 86 and 84 of the template. Probe 52 and sink 54 of reporter 50 may remain separate from one another (i.e., not base-paired) throughout amplification, if amplification is performed above the melting temperature of the reporter. Accordingly, sink 54 may not bind to probe 52 until after amplification has been completed.

Each of the forward and reverse primers then may be extended during the first cycle to produce primer extension products 92, 94 bound to respective strands 86 and 84 of template 80. During extension of the forward primer, the polymerase encounters probe 52 bound to strand 86 and catalyzes cleavage of probe oligonucleotide 58, to form degraded probe 70.

Additional cycles of amplification may be performed to generate amplicon 96 (interchangeably termed an amplified target), until an endpoint of amplification is reached. Each copy of amplicon 96 may have boundaries defined by primers 88 and 90, or other primers if, for example, nested amplification is performed. In any event, degraded probe 70 accumulates during amplification, while intact probe 52 is depleted. Accordingly, the amplitude (interchangeably termed the magnitude or the level) of the photoluminescence detectable from (and/or or dependent on) photoluminophore 60 is higher if at least one copy of template 80/target 82 is present in the partition before amplification. The difference in photoluminescence amplitude between a negative partition and a positive partition is increased because sink 54 is bound to probe 52 during detection if the probe is not degraded.

II. ASSAYS

This section describes exemplary amplification assays that may be performed with a sink and an exemplary system for performing a digital assay with a sink; see FIGS. 4 and 5.

FIG. 4 shows a flowchart of an exemplary method 110 of performing an assay or analysis. The steps presented for method 110 may be performed in any suitable order and in any suitable combination. Furthermore, the steps may be combined with and/or modified by any other suitable steps, aspects, and/or features of the present disclosure.

Volume Formation.

At least one volume may be prepared for assay of a target, indicated at 112. The at least one volume may include a template corresponding to the target, a probe, and a sink. The volume also may include reagents for amplification of the target, such as one or more primers, an amplification enzyme (e.g., a polymerase or ligase), dNTPs/NTPs, and the like. Further aspects of the composition of a reaction mixture constituting the at least one volume are described below in Section III.

Preparation of the reaction mixture may include or be described as preparation of a sample. Preparation of the sample may include any suitable manipulation of the sample, such as collection, dilution, concentration, purification, lyophilization, freezing, extraction, combination with one or more assay reagents, performance of at least one preliminary reaction to prepare the sample for one or more reactions in the assay, or any combination thereof, among others. Preparation of the sample may include rendering the sample competent for subsequent performance of one or more reactions, such as one or more enzyme catalyzed reactions and/or binding reactions.

In some embodiments, preparation of the sample may include combining the sample with reagents for amplification and for reporting whether or not amplification occurred. Reagents for amplification may include any combination of one or more primers for synthesis of an amplicon corresponding to the target, dNTPs and/or NTPs, at least one enzyme (e.g., a polymerase, a ligase, a reverse transcriptase, a restriction enzyme, or a combination thereof, each of which may or may not be heat-stable), and/or the like. Accordingly, preparation of the sample may render the sample (or partitions thereof) capable of amplification of each of one or more targets, if present, in the sample (or a partition thereof). Reagents for reporting may include a different reporter for each target of interest. Accordingly, preparation of the sample for reporting may render the sample capable of reporting, or being analyzed for, whether or not amplification has occurred, on a target-by-target basis, and optionally the extent of any such amplification.

Formation of the reaction mixture may include forming a continuous phase or bulk phase containing all of the components necessary for target amplification. Alternatively, or in addition, formation of the reaction mixture may include fusing partitions, such as droplets (see below).

The term "luminescence" means emission of light that cannot be attributed merely to the temperature of the emitting body. Exemplary forms of luminescence include photoluminescence, chemiluminescence, electroluminescence, or the like. A "luminophore" is any atom, associated group of atoms, moiety, molecule, or associated group of molecules capable of luminescence. Photoluminescence is any luminescence produced in response to irradiation with excitation light and includes fluorescence, phosphorescence, etc.

Accordingly, a luminophore may be a photoluminophore, such as a fluorophore or a phosphor, among others.

A target interchangeably may be termed an analyte, a species, or, in some cases, a template.

Partition Formation.

Partitions may be formed each containing a portion of the same reaction mixture and/or sample, and/or each containing a portion of an incomplete precursor to the reaction mixture (if the partitions are to be supplemented with one or more additional reaction components). Each target may be amplified from a template, such as from a single copy of the template if present in a given partition.

The partitions when provided (e.g., when formed) may contain a target at "partial occupancy," which means that one or more of the partitions do not contain at least one copy of the target. In other words, only a subset of the partitions contains at least one copy of the target. Accordingly, with partial occupancy, one or more (e.g., a plurality) of the partitions contain no copies of the target, one or more (e.g., a plurality) of the partitions may contain a single copy (only one copy) of the target, and, optionally, yet one or more of the partitions (e.g., the rest of the partitions) may contain two or more copies of the target.

The term "partial occupancy" is not restricted to the case where there is no more than one copy of a particular template/target of interest in any partition. Partitions containing a template and/or a target at partial occupancy may, for example, contain an average of more than, or less than, about one copy, two copies, or three copies, among others, of the template/target per partition when the partitions are provided or formed. Copies of a template (and/or target) may have a random distribution among the partitions, which may be described as a Poisson distribution.

Partition formation may involve distributing any suitable portion including up to all of the sample/reaction mixture to the partitions. Each partition may be and/or include a fluid volume that is isolated from fluid volumes of other partitions. The partitions may be isolated from one another by a fluid/liquid phase, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with at least one droplet generator having an orifice and/or a channel intersection at which droplets are created, by agitation of the sample/reaction mixture (e.g., shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 pL, among others.

Partitions competent for amplification of each target may be formed directly from a bulk phase containing the template, or may be formed in multiple steps. In some cases, the step of forming partitions may include dividing a bulk phase into isolated fluid volumes (such as droplets) containing the template at partial occupancy. The fluid volumes may be the partitions themselves or may contribute to the partitions. For example, the fluid volumes may be a first set of fluid volumes, and the step of forming partitions may include combining individual fluid volumes of the first set with individual fluid volumes of a second set. The second set may include one or more reagents for amplification of one or more of the targets, such as at least one primer for amplification of at least one of the targets, a probe, a sink, or the like. The step of combining may include fusing fluid volumes of the first set individually with fluid volumes of the second set, such as fusing droplets containing the template with droplets containing primers for amplification of one or more targets from the template.

Target Amplification.

Each target may be amplified, indicated at 114. Amplification may be performed in partitions (a dispersed phase) or in a continuous phase, such as in the reaction mixture without forming partitions. If performed in partitions, amplification of each target may occur selectively (and/or substantially) in only a subset of the partitions, such as less than about three-fourths, one-half, one-fourth, or one-tenth of the partitions, among others. Amplification of each target may occur selectively or exclusively in partitions containing at least one copy of the target (i.e., containing at least one copy of a template corresponding to the target).

Amplification may or may not be performed isothermally. In some cases, amplification in the partitions (and/or at least one volume) may be encouraged by heating the partitions (and/or volume) and/or incubating the partitions (and/or volume) at a temperature above room temperature, such as at a denaturation temperature (e.g., greater than about 90 degrees Celsius), an annealing temperature (e.g., about 50-75 degrees Celsius), and/or an extension temperature (e.g., about 60 to 80 degrees Celsius), for one or a plurality of cycles. In some examples, the partitions (and/or volume) may be thermally cycled to promote amplification by a polymerase chain reaction and/or ligase chain reaction, among others. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Light Detection.

Photoluminescence of the reporter may be detected, optionally below the reporter melting temperature, indicated at 116. Light detected may be emitted by the photoluminophore of the reporter directly or may be emitted by an energy transfer partner of the photoluminophore, among others. Detection of light may be described as collection of amplification data. The data may be collected by detecting light emitted from individual partitions or from the at least one volume. The light may be emitted in response to irradiation of the partitions or volume with excitation light for the photoluminophore. The data may be collected for emission of light from the partitions, or volume, in one wavelength/waveband (one optical channel), a pair of wavelengths/wavebands (two optical channels), or the like.

An optical channel may represent a particular detection regime with which emitted light is generated and detected. The detection regime may be characterized by a wavelength/waveband (i.e., a wavelength regime) for detection of emitted light. If pulsed excitation light is used in the detection regime to induce light emission, the detection regime may be characterized by a wavelength or waveband for illumination with excitation light and/or a time interval during which light emission is detected with respect to each light pulse. Accordingly, optical channels that are different from each other may differ with respect to the wavelength/waveband of excitation light, with respect to the wavelength/waveband of emitted light that is detected, and/or with respect to the time interval during which emitted light is detected relative to each pulse of excitation light, among others.

Data collection may include generating one or more signals representative of light detected from individual partitions or the reaction mixture. The signals may represent an aspect of light, such as the intensity, polarization, or lifetime of the light, among others. The signals optionally may include data collected in two or more different optical channels (e.g., in different wavelengths/wavelength ranges (wavebands) and/or color regimes) from probes/reporters for the same and/or different targets). The light detected from each probe/reporter may be light emitted by a photoluminophore (e.g., a fluorophore). The light detected in a given channel may be detected such that light from different probes/reporters is summed or accumulated without attribution to a particular probe/reporter. Thus, the signal for a given channel may be a composite signal that represents two, three, four, or more assays and thus two, three, four, or more targets. In other cases, the signals for the targets may be detected in different optical channels.

The signal(s) may be created based on detected light emitted from one or more probes/reporters in the partitions. The one or more probes/reporters may report whether at least one of two or more particular amplification reactions represented by the signal has occurred in a partition and thus whether at least one copy of at least one of two or more particular targets corresponding to the two or more particular amplification reactions is present in the partition. The level or amplitude of the signal corresponding to the reporters may be analyzed to determine whether or not at least one of the particular amplification reactions has occurred and at least one copy of one of the particular targets is present. The level or amplitude of the signal may vary among the partitions according to whether at least one of the particular amplification reactions occurred or did not occur and at least one of the particular targets is present or absent in each partition. For example, a partition testing positive for a particular target only may produce a signal value that is above a given threshold and/or within a given range. Partitions may be analyzed and signals created at any suitable time(s). Exemplary times include at the end of a reaction phase of the assay (an endpoint assay), when reactions have run to completion and the data no longer are changing, or at some earlier time, as long as the data are sufficiently and reliably separated.

The reporters may have any suitable structure and characteristics. Each reporter may be a probe including an oligonucleotide and a photoluminophore associated with the oligonucleotide (e.g., with the photoluminophore covalently attached to the oligonucleotide), to label the oligonucleotide. The probe also may or may not include an energy transfer partner for the photoluminophore, such as a quencher or another photoluminophore. The probe may be capable of binding specifically to an amplicon (e.g., a strand thereof) produced by amplification of a target. The probe may or may not also function as an amplification primer that forms part of an amplicon in the assay. Exemplary labeled probes include TaqMan@ probes, Scorpion® probes/primers, Eclipse® probes, Amplifluor® probes, molecular beacon probes, Lux® primers, proximity-dependent pairs of hybridization probes that exhibit FRET when bound adjacent one another on an amplicon, QZyme® primers, or the like.

In some cases, at least one of the reporters may be a generic reporter, such as a dye, that binds nucleic acid relatively nonspecifically. For example, the dye may have no covalent attachment to an oligonucleotide that confers substantial sequence binding specificity. The dye may be a major groove binder, a minor groove binder, an intercalator, or an external binder, among others. The dye may bind preferentially to double-stranded relative to single-stranded nucleic acid and/or may exhibit a greater change in a photoluminescent characteristic (e.g., intensity) when bound to double-stranded relative to single-stranded nucleic acid. Exemplary dyes that may be suitable include luminescent cyanines, phenanthridines, acridines, indoles, imidazoles, and the like, such as DAPI, Hoechst® 33258 dye, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others. Multiplexed assay of two or more targets may be performed in the same partitions with two or more distinct target-specific probes and/or at least one target-specific probe and a generic reporter.

Population Identification.

Partition populations (interchangeably termed clusters or bands) that test negative or positive for one or more targets may be identified from the data. Identification may be performed by a data processor using an algorithm (e.g., an algorithm that identifies patterns (e.g., partition clusters) in the data), by a user, or a combination thereof. In some cases, a data processor may produce and output (e.g., display) a plot of the collected data (e.g., a graph, a 2-D scatter plot, a histogram, or the like). The user then may define the boundary of each population based on the plot(s), e.g., through a graphical user interface to define population boundaries, or by inputting values (e.g., representing amplitude thresholds/ranges) to define a boundary for each population. Each population boundary may be defined by one or more ranges of values, a geometrical shape that surrounds the population (e.g., a polygon, ellipse, etc.), an algorithm, or the like. Accordingly, the population boundary may be determined by the user, automatically by a processor through an algorithm, or a combination thereof.

Identification of partition populations may include assigning each partition to one of a plurality of predefined bins each corresponding to a distinct partition population. The predefined bins may represent all combinations of negatives and positives for the targets.

Obtaining Partition Counts.

A partition count for each partition population may be obtained. The partition count may be a value representing the number of partitions constituting a particular partition population.

Determination of Target Property.

A property of at least one target may be determined based on the photoluminescence detected (i.e., on the collected data), indicated at 118. The property may be a level (e.g., a concentration), activity, configuration, location, or the like. The level may represent the level of target/template that was present before amplification. Determination of target levels may (or may not) be based on each target having a Poisson distribution among the partitions. Each level may, for example, be a value representing the total number of partitions positive (or negative) for the target/template/amplicon, or a concentration value, such as a value representing the average number of copies of the target/template per partition or unit volume, among others. The partition data further may be used (e.g., directly and/or as concentration data) to estimate copy number (CN) and copy number variation (CNV), or any other property of the sample, using any suitable algorithms.

A level (e.g., concentration) of each target may be determined with Poisson statistics. The concentration may be expressed with respect to the partitions (or reaction mixture) and/or with respect to a sample providing the target. The concentration of the target in the partitions may be calculated from the fraction of positive partitions (or, equivalently, the fraction of negative partitions) by assuming that copies of the target (before amplification) have a Poisson distribution among the partitions. With this assumption, the fraction f(k) of partitions having k copies of the template is given by the following equation:

$$f(k) = \frac{\lambda^k}{k!} e^{-\lambda} \qquad (1)$$

Here, $\lambda$ is the concentration of the target in the partitions, expressed as the average number of target copies per partition (before amplification). Simplified Poisson equations may be derived from the more general equation above and may be used to determine target concentration from the fraction of positive partitions. An exemplary Poisson equation that may be used is as follows:

$$\lambda = -\ln\left(1 - \frac{N_+}{N_{tot}}\right) \qquad (2)$$

where $N_+$ is the number of partitions (i.e., the partition count) positive for a given target, and where $N_{tot}$ is the total number of partitions that are positive or negative for the target. $N_{tot}$ is equal to a sum of (a) $N_+$ for the target and (b) the number of partitions negative for the target, or $N_-$. $N_+/N_{tot}$ (or $N_+/(N_++N_-)$) is equal to $f_+$, which is the fraction of partitions positive for the template (i.e., $f_+=f(1)+f(2)+f(3)+\ldots$) (see Equation 1), and which is a measured estimate of the probability of a partition having at least one copy of the template. Another exemplary Poisson equation that may be used is as follows:

$$\lambda = -\ln\left(\frac{N_-}{N_{tot}}\right) \qquad (3)$$

where $N_-$ and $N_{tot}$ are as defined above. $N_-/N_{tot}$ is equal to $f_-$, the fraction of negative partitions (or $1-f_+$), and is a measured estimate of the probability of a partition having no copies of the target, and $\lambda$ is the target concentration as described above.

Equations 2 and 3 above can be rearranged to produce the following:

$$\lambda = \ln(N_{tot}) - \ln(N_{tot}-N_+) \qquad (4)$$

$$\lambda = \ln(N_{tot}) - \ln(N_-) \qquad (5)$$

The concentration of each target in an assay can, for example, be determined with any of Equations 2 to 5, using values (i.e., partition counts) obtained for $N_{tot}$ and $N_-$ or, equivalently, $N_+$, for each target. In some cases, the value used for $N_{tot}$ (the total partition count) may be the same for each target. In other cases, the value used for $N_{tot}$ may vary, such as if some of the populations are excluded from the total count due to population overlap. In some embodiments, $N_{tot}$ may be equivalent to a combination of all populations, namely, a sum of the partition counts for all populations identified.

In some embodiments, an estimate of the level of a target (and/or the template) may be obtained directly from the positive fraction, without use of Poisson statistics. In particular, the positive fraction and the concentration (copies per partition) converge as the concentration decreases. For example, with a positive fraction of 0.1, the concentration is determined with Equation 2 to be about 0.105, a difference of only 5%; with a positive fraction of 0.01, the concentration is determined to be about 0.01005, a ten-fold smaller difference of only 0.5%. However, the use of Poisson statistics can provide a more accurate estimate of concentration, particularly with a relatively higher positive fraction, because Poisson statistics takes into account the occurrence of multiple copies of the same target/template in the same partition.

Further aspects of sample preparation, partition formation, data collection, population identification, obtaining partition counts, and target level determination, among others, that may be suitable for the system of the present disclosure are described elsewhere in the present disclosure, and in the references identified above in the Cross-References, which are incorporated herein by reference.

FIG. 5 shows an exemplary system 120 for performing the assay of FIG. 4. System 120 may include a partitioning assembly, such as a droplet generator 122 ("DG"), a thermal incubation assembly, such as a thermocycler 124 ("TC"), a detection assembly (a detector) 126 ("DET"), and a data processing assembly (a data processor) 128 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets) or signals/data, between the assemblies. Any suitable combination of the assemblies may be operatively connected to one another, and/or one or more of the assemblies may be unconnected to the other assemblies, such that, for example, material/data are transferred manually.

Detector 126 may provide a single channel or a plurality of optical channels in which data can be collected. The detector may have a distinct sensor or detection unit for each optical channel. The detector may be operatively associated with a light source configured to excite one or more photoluminophores of the assay.

System 120 may operate as follows. Droplet generator 122 may form droplets disposed in a continuous phase. The droplets may be cycled thermally with thermocycler 124 to promote amplification of one or more targets in the droplets. Signals may be detected from the droplets with detector 126. The signals may be processed by processor 128 to determine one or more droplet counts and/or target levels, among others.

III. COMPOSITIONS

This section provides exemplary compositions of the present disclosure. Each composition may or may not contain all the reagents necessary for amplification of a nucleic acid target.

The composition may be a continuous phase (interchangeably termed a bulk phase) or may be composed of partitions that are isolated from one another. If composed of partitions, the partitions may be aqueous partitions separated from one another by a solid phase (e.g., at least one wall of at least one container) and/or by a liquid phase, among others. The liquid phase may be a nonaqueous continuous phase that surrounds each of the partitions. The continuous phase may include at least one surfactant.

The nonaqueous phase may serve as a carrier fluid forming a continuous phase that is immiscible with water. The nonaqueous phase may be an oil phase comprising at least one oil, but may include any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil is hydrophobic and may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others.

In exemplary embodiments, the oil is a fluorinated oil, such as a fluorocarbon oil, which may be a perfluorinated organic solvent. A fluorinated oil may be a base (primary) oil or an additive to a base oil, among others. Exemplary fluorinated oils that may be suitable are sold under the trade name FLUORINERT (3M), including, in particular, FLUORINERT Electronic Liquid FC-3283, FC-40, FC-43, and FC-70. Another example of an appropriate fluorinated oil is sold under the trade name NOVEC (3M), including NOVEC HFE 7500 Engineered Fluid.

The composition may comprise any suitable combination of a template, at least one probe, at least one sink, one or more primers (at least one of which also may be a probe or a sink), dNTPs and/or NTPs, a polymerase (e.g., a heat stable polymerase), a ligase, a reverse transcriptase, water, buffer, and a carrier fluid that is immiscible with water, among others.

The template may be a nucleic acid, such as DNA and/or RNA, and may be at least predominantly single-stranded or double-stranded, among others. The template may be fragmented to any suitable size or size range.

The probe may include any combination of an oligonucleotide, at least one photoluminophore and at least one quencher for the photoluminophore. The oligonucleotide may be complementary to a region of an amplicon such that the oligonucleotide can bind to the amplicon during target amplification that generates the amplicon. The region of the amplicon may or may not be present in the template/target from which the amplicon is generated. Each of the photoluminophore and the quencher may be conjugated to the oligonucleotide. The quencher may be positioned (in the absence of a sink) for dynamic quenching and/or contact quenching.

The sink may bind the probe to affect an ability of at least one photoluminophore of the probe to emit light. For example, the sink may function to bring an energy transfer partner closer to the photoluminophore of the probe. The sink may include an oligonucleotide that is complementary to the probe, and also may include at least one energy transfer partner (such as a quencher) for the photoluminophore. Accordingly, the sink may bind the probe to position an energy transfer partner of the sink closer to the photoluminophore of the probe, and/or to position an energy transfer partner of the probe closer to the photoluminophore of the probe. If the sink lacks an energy transfer partner, the sink may have a 5'-portion that binds a 5'-portion of the probe and may have a 3'-portion that binds a 3'-portion of the probe (e.g., see Example 5).

The one or more primers may be configured to prime synthesis of at least one amplicon strand and/or complementary amplicon strands. The one or more primers thus may bind to the template and/or the amplicon and may define the ends of the amplicon. In exemplary embodiments, the one or more primers are a sense primer and a distinct antisense primer that collectively define the ends of the amplicon.

IV. EXAMPLES

This section describes selected aspects and embodiments of the present disclosure related to assays with a reporter including a sink. Any suitable aspects of the assay and reporter configurations disclosed in the section may be combined with one another and/or with aspects of assay and reporter configurations disclosed elsewhere in the present disclosure. These examples are intended for illustration only and should not limit or define the entire scope of the present disclosure.

Example 1. Sink for a Primer

Figure 7:
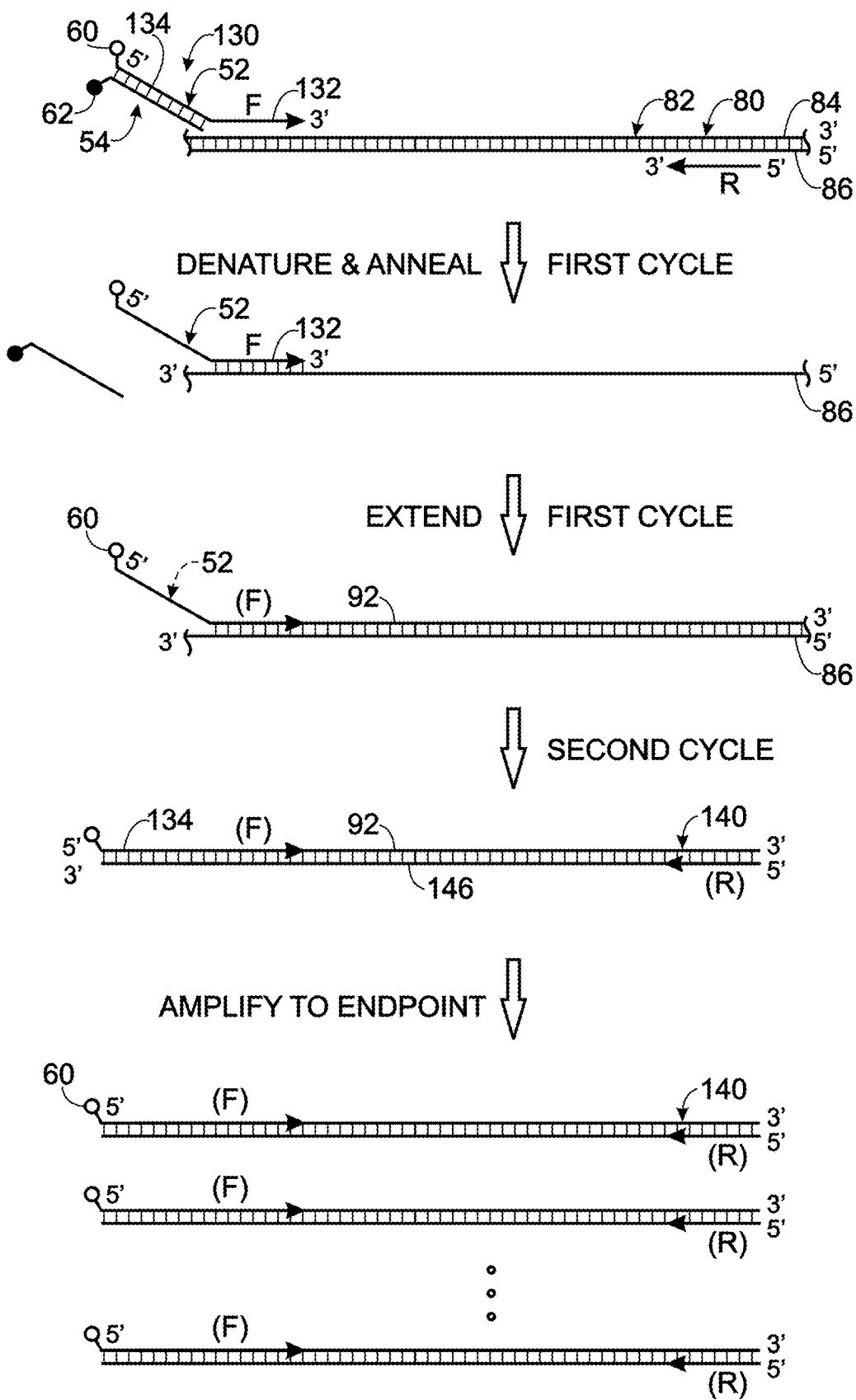
FIG. 7 is a schematic flowchart illustrating selected steps and configurations of an exemplary assay performed with the reporter of FIG. 6, in accordance with aspects of the present disclosure.

This example describes an exemplary assay performed with a sink capable of binding to a probe that functions as a labeled amplification primer; see FIGS. 6, 7, and 7A.

FIG. 6 shows a schematic comparing levels of fluorescence in an assay performed with an exemplary reporter 130 including a labeled primer (probe 52) that binds to a sink 54. Primer oligonucleotide 58 may (or may not) have a 3' priming region 132 that is dedicated to binding to a target and which has no complementarity to oligonucleotide 64 of sink 54. Priming region 132 (and/or primer oligonucleotide 58) can bind to a template/target at an annealing temperature to permit polymerase-mediated primer extension during amplification. The priming region may, for example, have a length of at least about 10, 15, or 20 nucleotides, among others. Oligonucleotide 58 also may have a 5' sink-binding region 134 that is dedicated to binding to sink 54 and which forms hydrogen bonds with the, to position photoluminophore 60 of sink-binding region 134 proximate to a quencher 62 at a lower temperature used for detection. Accordingly, the background level of fluorescence measured from the photoluminophore of reporter 130 may be low. Sink-binding region 134 may, for example, have a length of at least about 5, 10, or 15 nucleotides, among others. In some examples, regions 132 and 134 may overlap substantially or completely. Sink-binding region 134 may or may not be complementary to a template containing the target to be amplified.

Amplification of a target with probe 52 as a primer (and optionally at least one other primer) may generate an amplicon 140. A strand 142 of amplicon 140 binds to the extended probe and prevents sink 54 from binding to the extended probe 52 at a lower temperature that may be used for detection, indicated at 144. Since quencher 62 is not held proximate photoluminophore 60 during detection, the level of fluorescence measured from the photoluminophore incorporated into amplicon 140 may be relatively high compared to the background level of fluorescence for the reporter.

In other words, the extended probe may preferentially bind to the longer, complementary amplicon strand, due to the higher melting temperature of the resulting reporter, and not to the sink. In partitions where amplification does not occur, the non-extended probe may be bound at the detection temperature by the sink, which may quench emission of light from the probe. Assays based on this approach may be referred to as Amplicon Mediated Probe assays (AMP assays).

FIG. 7 shows selected steps and configurations of an exemplary assay that may be performed in partitions with reporter 130 of FIG. 6. The configurations shown here may be produced in a partition that contains at least one copy of template 80 containing target 82. The template may be double-stranded with strands 84 and 86, as shown, or single-stranded. A forward primer ("F") (i.e., probe 52 from reporter 130) and a reverse primer ("R"), are shown at the top of FIG. 7, aligned with corresponding regions of template 80/target 82 at which each can bind (after the template/target is denatured). Sink 54 may be in molar excess relative to probe 52, such that substantially all of the probe is bound to the sink at room temperature before amplification (and unbound copies of sink 54 may be present in the partition).

A first cycle of target amplification may be initiated by heating template 80 above its denaturation temperature. Annealing then may be performed at a temperature that permits probe 52 (and particularly priming region 132) to bind specifically to single strand 86 of the template. Binding of the reverse primer to strand 84 also occurs during the first cycle but is not illustrated here to simplify the presentation.

Each of the forward and reverse primers then may be extended during the first cycle to produce primer extension products bound to respective strands of template 80. Depicted extension product 92 may be generated by elongation of the forward primer (probe 52) with strand 86 serving as a template.

A second cycle of target amplification may be performed to generate a complete copy of amplicon 140 using extension product 92 as template. After denaturation, the reverse primer binds to extension product 92 and may be elongated. Accordingly, an extension product 146 incorporating the reverse primer can be elongated to a position aligned with the 5'-end of product 92, causing sink-binding region 134 of product 92 to be unavailable for later binding to sink 54, when the temperature is reduced. Additional cycles of amplification may be performed to increase the number of copies of amplicon 140 until an endpoint of amplification is reached. Successful amplification causes a decrease in the amount of quenched reporter 130 present during detection, generally in direct relation to the amount of photoluminophore-labeled amplicon 140 generated.

FIG. 7A shows an exemplary thermal profile for stages of the assay of FIGS. 6 and 7, and the status of reporter 130 (e.g., annealed, denatured, and/or covalently modified) during each stage. The stages identified on the horizontal axis of the graph are volume formation, thermocycling (and/or amplification), and detection. The thermal profile described here and below may apply to any of the reporter and assay configurations of the present disclosure.

Volume formation generally includes formation of one or more volumes for use in the amplification stage and/or detection stage. The formation of at least one volume may include mixing amplification reagents and sample and/or dividing a bulk volume including amplification reagents and/or sample into partitions (e.g., droplets). Volume formation may (or may not) be performed below the melting temperature of the reporter, at one more different temperatures. For example, a bulk volume may be formed by mixing a sample and reagents below room temperature (such as on ice). The bulk volume then may (or may not) be divided into partitions at room temperature (e.g., about 20-25 degrees Celsius) or below room temperature, among others. In any event, partitions may be formed below the melting temperature of the reporter, such that the reporter remains in a base-paired form 150, during partition formation (and/or bulk volume formation).

Amplification may be performed by incubating the at least one volume at a single temperature or two or more different temperatures above the melting temperature of the reporter. Accordingly, incubation may be isothermal or may include thermally cycling (i.e., thermocycling) the at least one volume, through a plurality of thermal cycles (also called amplification cycles), such as at least 5, 10, or 15 cycles, among others. The at least one volume may remain above the melting temperature of the reporter during an annealing portion and/or a primer extension portion of each amplification cycle. The reporter may be in a separated form 152 during any suitable portion of each amplification cycle, such as throughout each of a plurality of amplification cycles. At least a portion of the reporter, probe, and/or sink may be covalently modified by amplification, such as extended to form extension product 92 and/or cleaved to form a degradation product.

Detection of light from reporter 130 may be performed below the melting temperature of the reporter. A portion that the reporter that is not modified during amplification may be present in base-paired form 150. Another portion of the reporter may be present in a separated form created by base-pairing of extension product 92 with complementary extension product 146 of amplicon 140, with sink 54 left unpaired.

Example 2. Reporter with a Single Quencher

Figure 8:
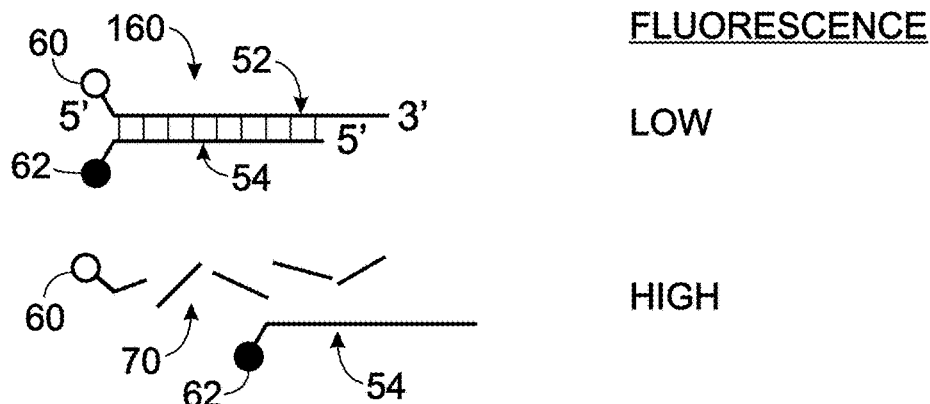
FIG. 8 is a schematic comparing levels of fluorescence produced by (a) yet another exemplary reporter including a probe and a sink that base-pair with one another, and (b) the probe of the reporter degraded as a result of target amplification, in accordance with aspects of the present disclosure.

This example describes an exemplary reporter in which the probe contains no quencher, with the probe being degraded during target amplification; see FIG. 8.

FIG. 8 shows a schematic comparing levels of fluorescence in an assay performed with a reporter 160 including a probe 52 that does not have a covalently linked quencher (compare with FIG. 1). Sink 54 provides a quencher 62, which may provide sufficient quenching as the only quencher moiety in the reporter, to give a low fluorescence background signal. Degraded probe 70, generated as a byproduct of amplification, produces a relatively high fluorescence signal because quencher 62 of sink 54 is no longer held proximate photoluminophore 60.

Example 3. Reporter with Sink Degradation

Figure 9:
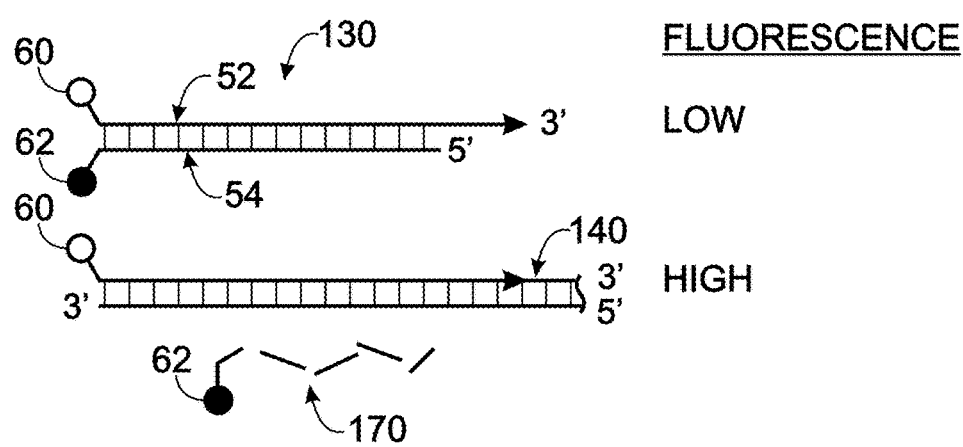
FIG. 9 is a schematic comparing levels of fluorescence from (a) a higher melting-temperature version of the reporter of FIG. 6, and (b) a polymerase-extended version of a probe from the reporter, with the probe forming part of an amplicon and with a sink of the reporter cleaved as a result of target amplification, in accordance with aspects of the present disclosure.

This example describes an exemplary reporter in which a probe is an amplification primer and contains no quencher, with a sink of the reporter being degraded during target amplification; see FIG. 9.

FIG. 9 shows a schematic comparing levels of fluorescence in an assay performed with a more stable version of reporter 130 of FIG. 6 and a polymerase capable of catalyzing cleavage of sink 54 during target amplification. Reporter 130 may, for example, be more stable than in FIG. 6 because sink 54 may be longer (compare FIGS. 6 and 9). The reporter may be sufficiently stable to form during the annealing step of an amplification cycle and to remain base-paired during the extension step of the cycle. Partitions lacking a copy of the target exhibit a low level of background fluorescence because sink 54 of reporter 130 remains intact. Partitions having at least one copy of the target exhibit a relatively high level of fluorescence; formation of amplicon 140 results in a degraded form 170 of sink 54 that cannot quench photoluminophore 60 efficiently.

Example 4. Amplification Primer as a Sink

Figure 9A:
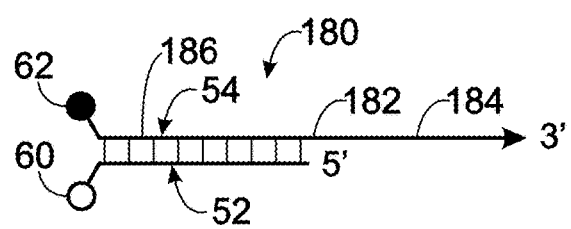
FIG. 9A is a schematic view of an exemplary reporter including a sink having a quencher and base-paired with a probe, with the sink configured to function as a polymerase-extendable primer for amplification, in accordance with aspects of the present disclosure.

This example describes an exemplary reporter 180 in which sink 54 is configured as an amplification primer; see FIG. 9A.

Reporter 180 may be structured generally as described above for reporter 130 of FIG. 6, except that the positions of a photoluminophore 60 and a quencher 62 are reversed. In particular, quencher 62 may be conjugated to a primer oligonucleotide 182. Oligonucleotide 182 may have a priming region 184 and a probe-binding region 186, each of which may be structured as described above for counterpart regions of oligonucleotide 58 of FIG. 6. (For example, probe-binding region 186 may be completely contained in priming region 184.) Quencher 62 may be attached to either region and at any suitable position along the region. A probe 52 of the reporter may bind region 186 of oligonucleotide 182. Probe provides photoluminophore 60 and may or may not be complementary to the amplicon produced by amplification. Quenching of photoluminophore 60 may be diminished if the probe is degraded during amplification (if reporter 180 is stable enough to be present during amplification) and/or if the probe is excluded from binding to extended sink 54 at a detection temperature by amplicon formation.

Example 5. Sink without a Quencher

Figure 10:
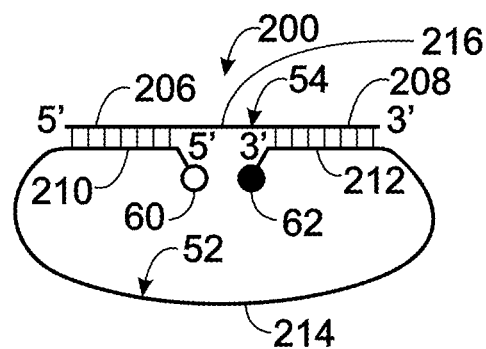
FIG. 10 is a schematic view of an exemplary reporter including a sink base-paired with a probe, with the probe arranged to quench photoluminescence intramolecularly as a result of binding to the sink, in accordance with aspects of the present disclosure.
Figure 11:
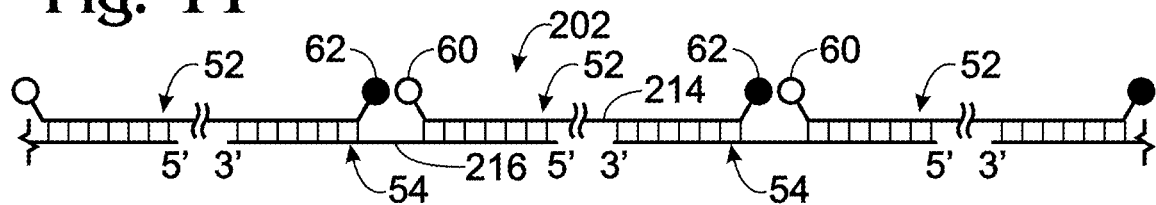
FIG. 11 is a schematic view of an exemplary reporter including a sink bound to a probe, with the probe arranged to quench photoluminescence intermolecularly as a result of binding to the sink, in accordance with aspects of the present disclosure.

This example describes exemplary reporters 200, 202 in which probe 52 is placed in a quenched configuration by a sink 54 containing no quencher; see FIGS. 10 and 11.

Sink 54 may be structured as an oligonucleotide that is not conjugated to a quencher (or a photoluminophore). The oligonucleotide may include a 5'-portion 206 and a 3'-portion 208 that are respectively complementary to and bind to a 5'-portion 210 and a 3'-portion 212 of probe 52. As a result, a photoluminophore 60 and a quencher 62 of the probe are held in proximity to each other in the reporter, reducing the basal luminescence of the probe, such as by contact quenching. Sink 54 may have a 3'-phosphorylation or other modification or structure to prevent extension of the sink, which could cause probe cleavage. The sink also or alternatively may be structured to be resistant to polymerase-mediated cleavage.

The length of probe 52 may determine whether the probe is preferentially circularized to form a circular hybrid of reporter 200, which is quenched intramolecularly, or arranged generally end-to-end in series, to form a chain hybrid of reporter 202 (interchangeably termed a linear hybrid), which is quenched intermolecularly. Circular hybrid 200 uses the same copy of probe 52 to provide a copy of photoluminophore 60 and a copy of quencher 62 that quenches the photoluminophore copy. Chain hybrid 202 uses a pair of copies of probe 52 to provide a copy of quencher 62 that quenches a copy of photoluminophore 60. The length of a spacer region 214 of probe 52 that extends from end region 210 to end region 212 can determine whether the probe preferentially forms hybrid 200 or 202. For example, if the spacer region is long enough, as in FIG. 10, the same copy of the probe can bind to distinct regions of the same copy of sink 54. If the spacer region is not long enough for probe circularization, the chain hybrid of FIG. 11 may be formed instead. In some cases, spacer region 214 may be short, such as no more than four, three, two, or one nucleotide, to optimize the quenching of the photoluminophore by the quencher (e.g., such that contact quenching occurs). Sink 54 also may have a spacer region 216 that connects end portions 206 and 208. Spacer region 216 may be kept short, such as no more than four, three, two, or one nucleotide, to optimize quenching of the photoluminophore by the quencher (e.g., such that contact quenching occurs).

Example 6. Reporter with Nonterminal Photoluminophore and Quencher

Figure 12:
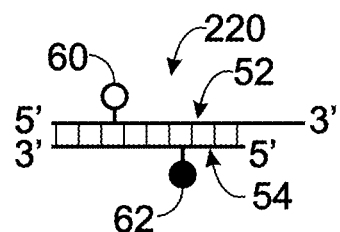
FIG. 12 is a schematic view of an exemplary reporter including a sink bound to a probe, with a photoluminophore of the probe and a quencher of the sink each positioned intermediate the opposing ends of the probe or sink, in accordance with aspects of the present disclosure.

This example describes an exemplary reporter 220 formed by a probe 52 and a sink 54 providing a photoluminophore 60 and a quencher 62 at nonterminal positions along respective oligonucleotides of the probe and sink; see FIG. 12. In other embodiments, one member of an energy transfer pair may be located at a terminal position (conjugated to the 5'- or 3'-end of an oligomer chain), and the other member of the energy transfer pair may be disposed at a nonterminal position of the same oligomer chain or at a nonterminal position of an at least partially complementary oligomer chain.

Example 7. Assay of a Target Region with at Least Two Probes

Figure 13:
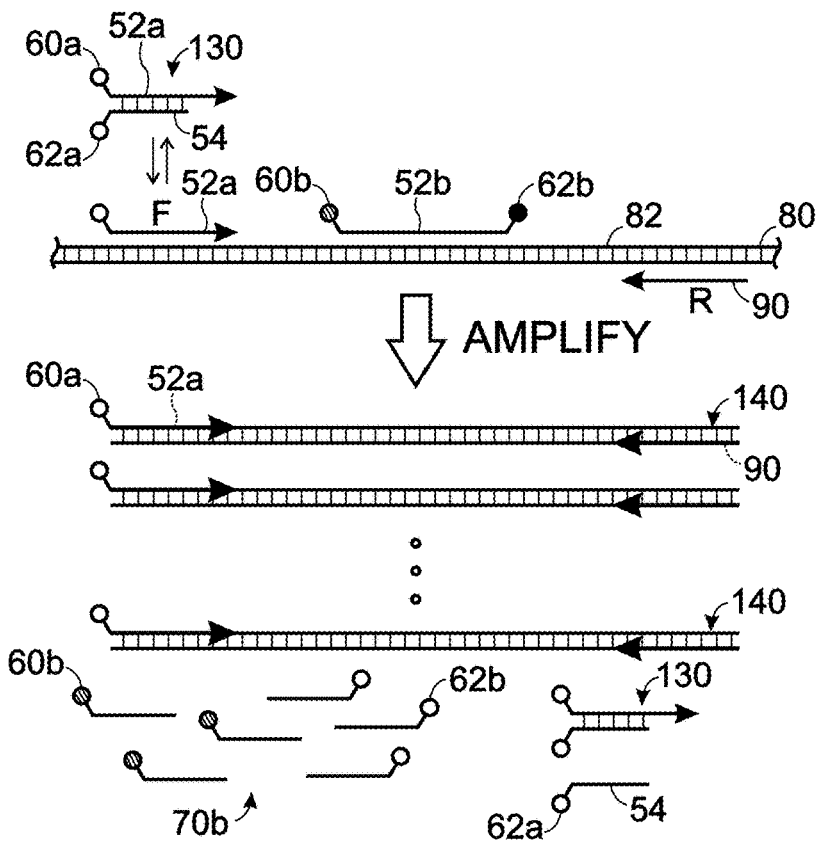
FIG. 13 is a schematic flowchart illustrating a strategy for assay of a target region using at least two distinct probes, with at least one of the probes being a primer bound by a sink at room temperature and another of the probes being self-quenched intramolecularly, in accordance with aspects of the present disclosure.
Figure 14:
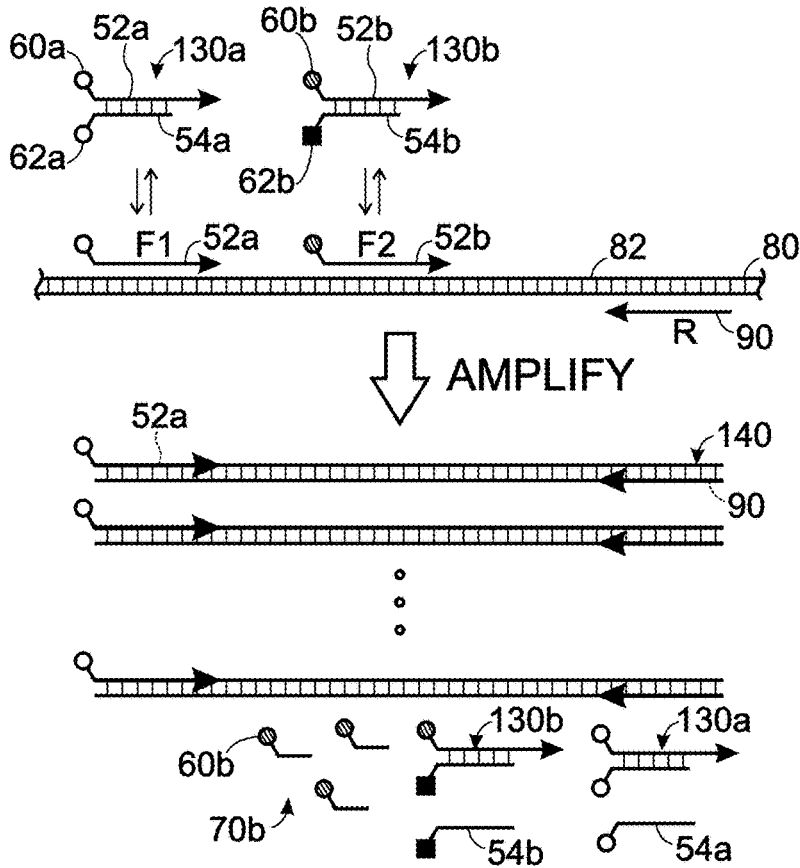
FIG. 14 is another schematic flowchart illustrating another strategy for assay of a target region using at least two distinct probes, with each of the probes being a primer bound by a different sink at room temperature, in accordance with aspects of the present disclosure.

This example describes exemplary strategies for assaying a target region using at least two distinct probes and at least one sink; see FIGS. 13 and 14.

FIG. 13 is a schematic flowchart illustrating a strategy for assay of a target or target region using at least two distinct probes 52a and 52b. The strategy may be performed in partitions, such as droplets, or may be performed in a bulk phase.

Probe 52a may be a primer labeled with a photoluminophore 60a. The probe may be complementary to a sink 54 to form a reporter 130 at the detection temperature, but not at the annealing temperature used for amplification. Probe 52a may be configured to bind to a template 80 providing a target 82.

Probe 52b may be a self-quenching probe having a photoluminophore 60b and a quencher 62b for the photoluminophore. Photoluminophores 60a and 60b may be optically distinguishable, such as having distinct emission spectra. A sink capable of binding to probe 52b may or may not be present.

Amplification of target 82 with probe 52a and reverse primer 90 (R) produces copies of amplicon 140 each labeled with photoluminophore 60a. Amplification also may produce degraded probe 70b from probe 52b, such that photoluminophore 60b is no longer quenched by quencher 62b. At the detection temperature, after amplification, positive partitions may contain labeled amplicon 140, degraded probe 70b, and sink 54, and optionally may contain intact probe 52b (a remaining amount not degraded during amplification) and/or reporter 130 (including copies of probe 52a not used for amplification). The positive partitions may have a distinctive luminescence signature produced by light emitted by photoluminophores 60a and 60b. Negative partitions may contain substantially more reporter 130 and intact probe 52b than positive partitions. In some cases, other targets may be assayed in the same partitions using probes labeled with only photoluminophore 60a or only photoluminophore 60b.

FIG. 14 shows another schematic flowchart illustrating another strategy for assay of a target or target region using at least two distinct probes 52a and 52b. The strategy may be performed in partitions, such as droplets, or may be performed in a bulk phase.

Each of probes 52a and 52b may be a forward primer (F1 and F2) labeled with a distinct photoluminophore 60a or 60b. Each probe 52a and 52b may be at least partially complementary to a respective sink, 54a and 54b, to form a base-paired form of reporters 130a, 130b at the detection temperature, but not at the annealing temperature used for amplification. Sinks 54a and 54b may contain quenchers 62a and 62b, which may be copies of each other or structurally different (as shown here). Each probe 52a and 52b may be configured to bind to a template 80 providing a target 82, and may be extendable by polymerase. The probes may bind to the same strand or respective complementary strands of the template. In some cases, the probes may function as respective sense and antisense primers that define the ends of a corresponding amplicon.

Amplification of target 82 with probe 52a and reverse primer 90 (R) produces copies of amplicon 140 each labeled with photoluminophore 60a. Amplification also may produce degraded probe 70b from probe 52b, such that photoluminophore 60b is no longer quenched by quencher 62b. The base-paired configuration of reporters 130a and 130b may be present after amplification at a detection temperature, in amounts inversely related to the extent of target amplification.

Figure 14A:
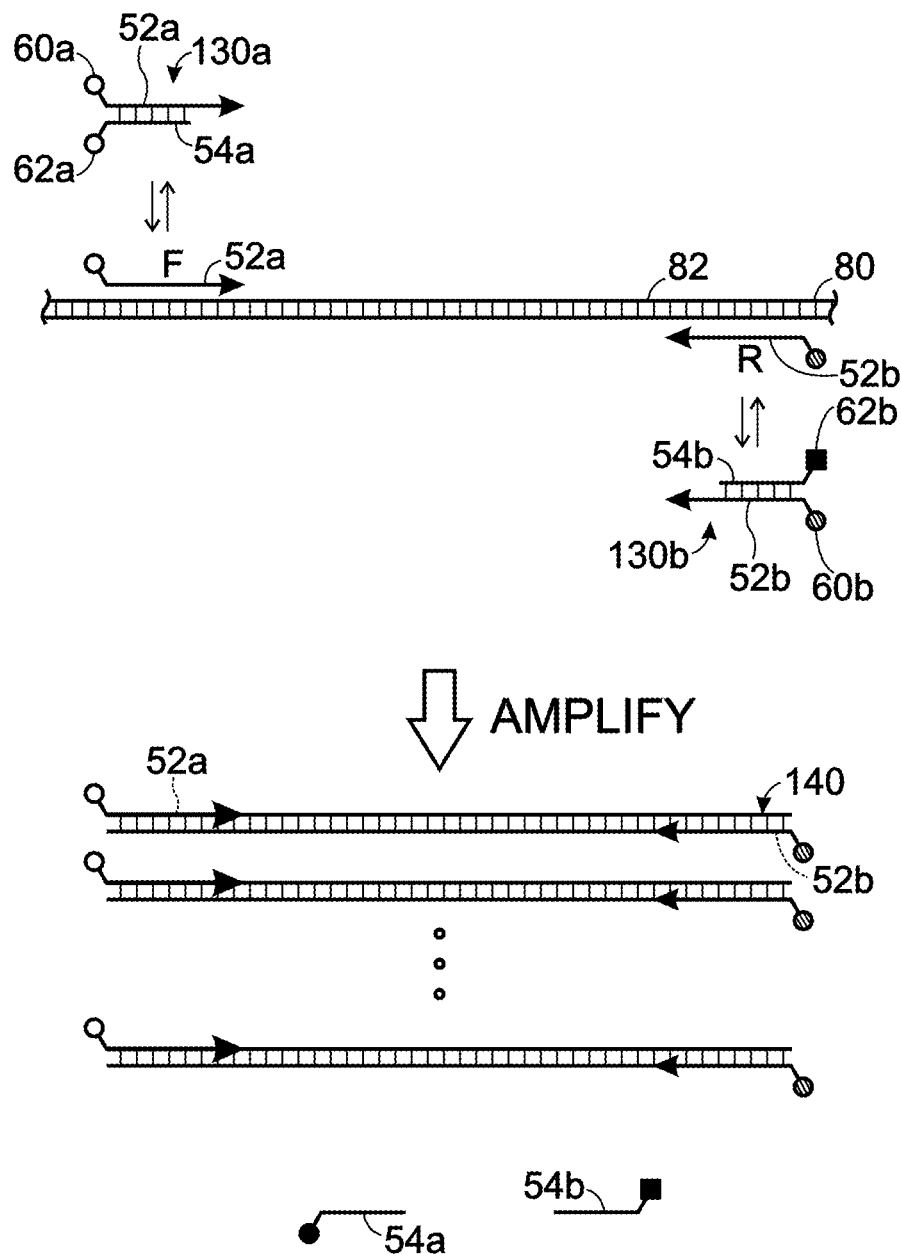
FIG. 14A is still another schematic flowchart illustrating still another strategy for assay of a target region using at least two distinct probes, with each of the probes being a forward or reverse primer bound by a different sink at room temperature, in accordance with aspects of the present disclosure.

FIG. 14A shows still another strategy for assay of a target using at least two distinct probes 52a and 52b (of respective reporters 130a, 130b). The strategy of FIG. 14A is similar to that of FIG. 14 except that probes 52a, 52b are configured as a forward primer (F) and a reverse primer (R), respectively, instead of as two different forward primers. Each probe may be bound by a sink 54a or 54b that affects photoluminescence of a respective different photoluminophore 60a or 60b. Amplification of the target may be detectable as a change in photoluminescence from both reporters 130a and 130b (e.g., from both photoluminophores 60a and 60b). This strategy may be utilized to achieve multiplexing to detect a plurality of different target sequences, such as in the same set of partitions. As an example, the primers for five different targets may be labeled as follows with four different photoluminophores (FAM, HEX, NED, and ALEXA 568), and each may be base-paired above the detection temperature with a respective sink:

| Target No. | Label (Forward Primer) | Label (Reverse Primer) |
|---|---|---|
| 1 | FAM | None |
| 2 | None | HEX |
| 3 | FAM | HEX |
| 4 | FAM | NED |
| 5 | FAM | ALEXA 568 |

Photoluminescence from the various photoluminophores may be detected in one or more wavelength regimes, such as in a pair of detection channels representing different wavelengths, to allow generation of a two-dimensional plot of the photoluminescence data. Each of the different combinations of the photoluminophores may produce a distinguishable target-positive cluster for each different target in the plot.

Example 8. Selectively Quenching a Primer Dimer

Figure 15:
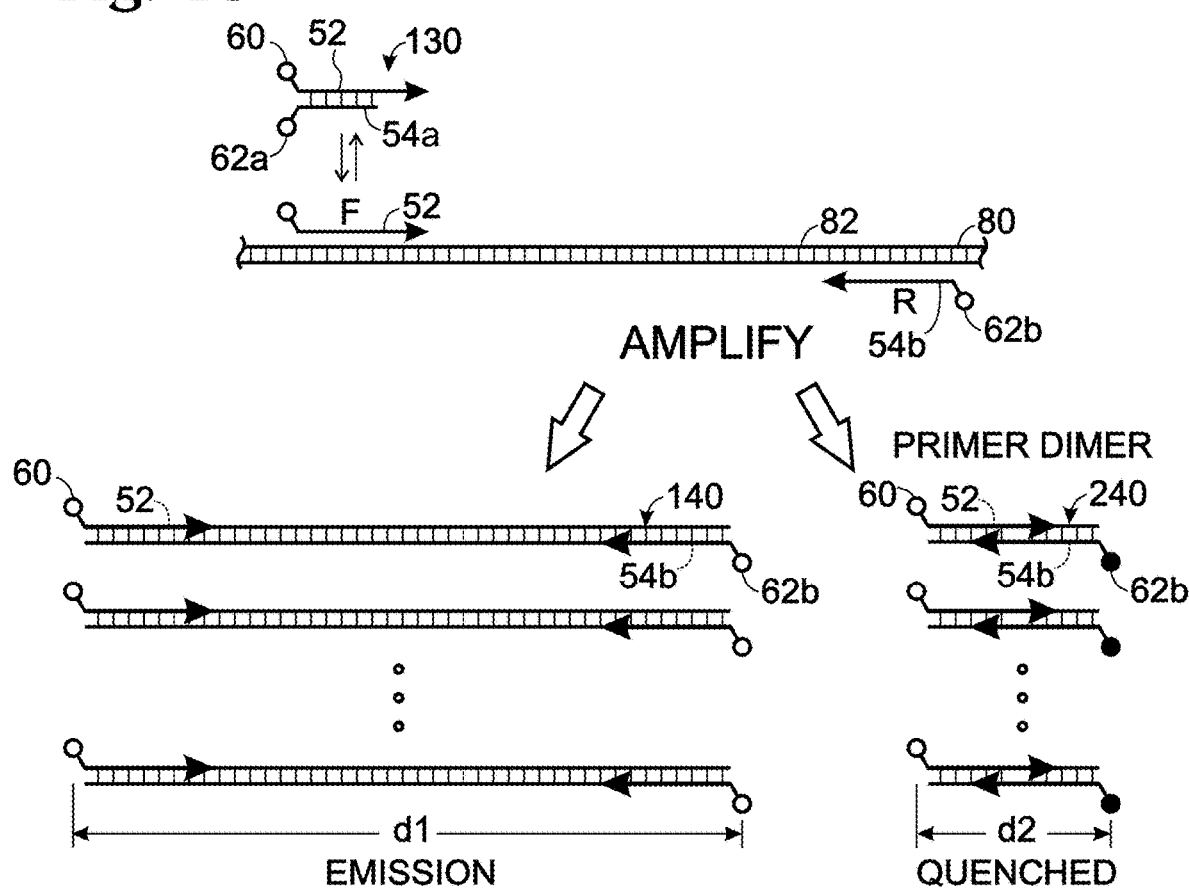
FIG. 15 is a schematic flowchart illustrating a strategy for selectively quenching emission of light from a primer dimer relative to a desired amplicon in an amplification assay performed with a photoluminophore-labeled primer as a probe, in accordance with aspects of the present disclosure.

This example describes an exemplary strategy for a target assay performed with a primer containing a quencher, to selectively quench light emission from a primer dimer 240 relative to a desired amplicon 140; see FIG. 15.

The formation of a primer dimer in an amplification assay, generally as an unwanted side-reaction product, can increase the noise and decrease the accuracy of the assay. FIG. 15 show a strategy for reducing the signal produced by a primer dimer in partitions (or a bulk volume). Amplification of a target 82 may be performed with a probe 52 serving as a forward primer (F), and a sink 54b configured to act as a reverse primer (R) and containing a quencher 62b for a photoluminophore 60 of the probe. Two exemplary products labeled with photoluminophore 60 may be produced, namely, amplicon 140 and primer dimer 240. Each of the products also contains quencher 62b. However, the respective average distance, d1 and d2, between the photoluminophore and quencher may be substantially greater in amplicon 140 than in primer dimer 240. Accordingly, emission of light from amplicon 140 is quenched much less than emission of light from primer dimer 240. As a result, target-negative partitions containing only primer dimer are less likely to be erroneously assigned as target-positive, which may improve the accuracy of the assay.

The idea is to intentionally lower the luminescence of primer dimers so they do not have the ability to affect quantification of the target. In other words, if a droplet that is somewhat positive due to primer dimer luminescence is classified as a positive droplet, this is not desirable as it affects quantification. The strategy described here can reduce the luminescence of primer dimer containing droplets and allows for more accurate target quantification.

The reverse primer has a quencher on it. For normal-sized amplicons, the distance between the quencher and the photoluminophore on the other primer is so great that little or no quenching occurs. In contrast, if the primer creates a primer dimer, then the distance is short enough that quenching occurs, and the droplets have lower luminescence and are correctly classified as negative for the target.

Example 9. Comparison of Background Signals in Singleplex and Multiplex Assays

Figure 16:
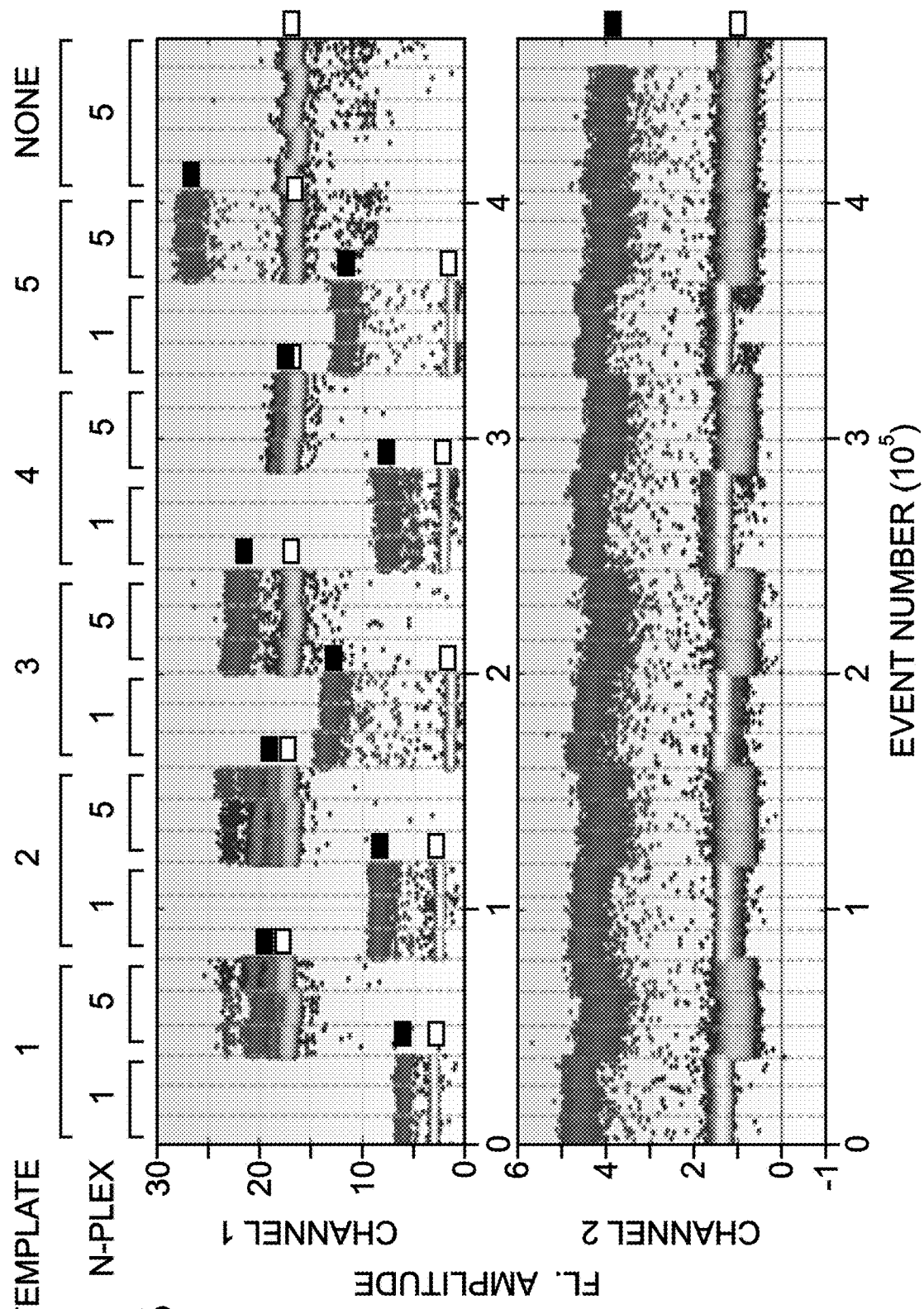
FIG. 16 is a plot of fluorescence amplitude measured for a series of assays performed in droplets, and showing changes in the basal fluorescence of negative droplets, and differences in the fluorescence amplitude between negative and positive droplets, for various targets and with different levels of assay multiplexing.
Figure 17:
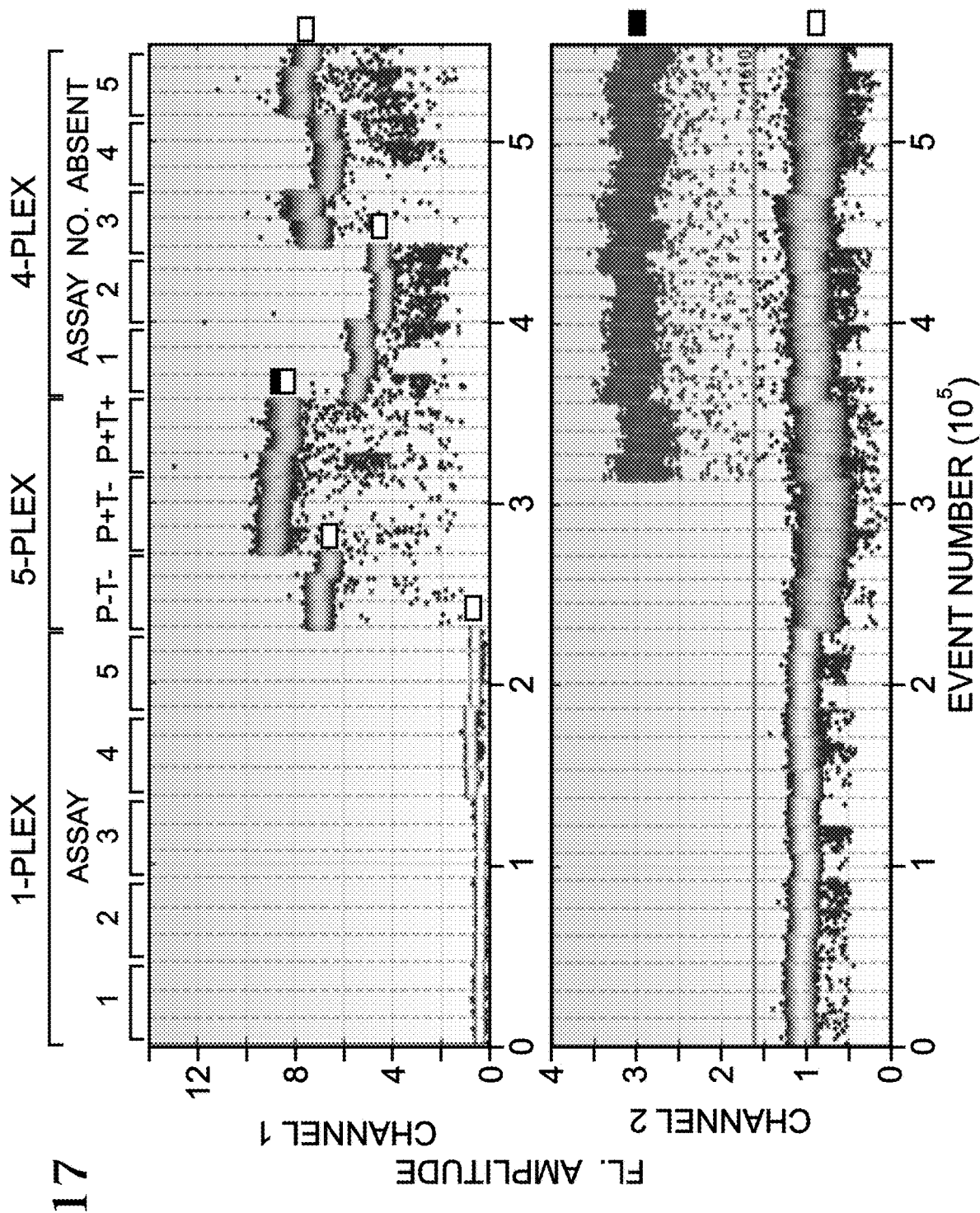
FIG. 17 is a plot of fluorescence amplitude measured for a series of assays performed in droplets, and showing changes in the basal fluorescence of negative droplets for various assay combinations, different levels of assay multiplexing, and/or with a different primer pair omitted from the assay.
Figure 18:
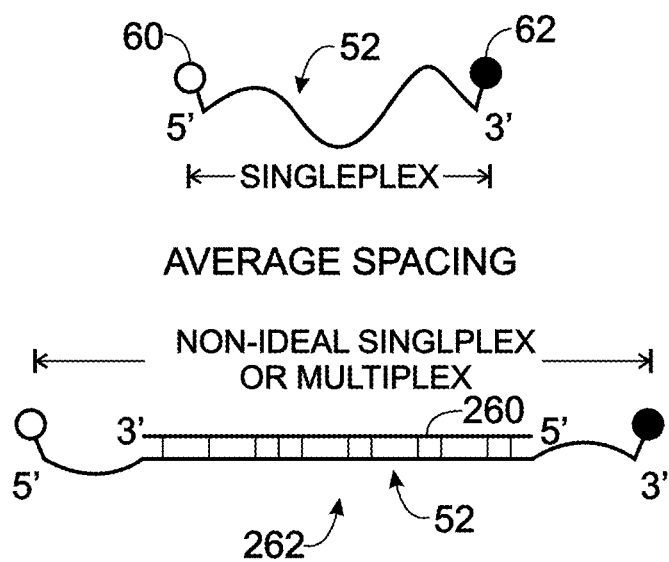
FIG. 18 is a schematic view of a probe in an ideal singleplex assay versus a probe in a non-ideal singleplex or multiplex assay, illustrating a possible change in average spacing between a photoluminophore and a quencher of the probe in the two assays, in accordance with aspects of the present disclosure.

This example describes exemplary data collected in singleplex and multiplex assays performed with various combinations of primers and templates; see FIGS. 16-18.

Maintaining a good signal-to-noise ratio in multiplex analysis can be challenging. FIG. 16 shows a pair of plots of fluorescence intensity signals (fluorescence (fl.) amplitude) detected from droplets traveling through a detection region. Each droplet detected may generate a characteristic fluorescence profile termed an "event," which is plotted in FIG. 16 (and FIGS. 17 and 19) according to the order in the events were detected. In other words, the first event detected is plotted as event number one, the second event as event number two, and so on, with fluorescence amplitude plotted in FIG. 16 for over $4 \times 10^5$ events (droplets). For each droplet, the fluorescence amplitude measured in each of two detection channels, channel 1 and channel 2, is plotted. Channel 1 (the "FAM channel") represent signals detected from one (1-plex) or five probes (five-plex) containing a FAM dye, and channel 2 ("the HEX channel") represents signals detected from a single probe containing a HEX dye in a single target assay. The data collected in the HEX channel serves as a control.

The data shown in the top plot was obtained with singleplex assays (each assay is designed to amplify and detect only one target) and multiplex assays (each assay is a combination of assays designed to amplify and detect multiple targets. The two types of assays are identified above the top plot in the row labeled "N-plex," with "1" indicating a singleplex assay and "5" indicating a multiplex assay for five targets. Each singleplex target assay and corresponding template has been assigned a number for one to five. The particular single template added to each assay, to generate amplification-positive droplets, is identified in the row labeled "template." Accordingly, each of templates "1" through "5" was added individually to a singleplex assay for the corresponding target, and was the only template added to a five-plex assay for all of targets 1 to 5. In other words, amplification of each of templates 1 to 5 was compared in a singleplex assay and a five-plex assay, to test the effect of multiplexing on the background signal and signal-to-noise ratio. The band of droplets negative for the particular template being tested is identified immediately to the right of each negative droplet band with an empty rectangle, and the droplets positive for the template with a filled rectangle.

Each of the singleplex assays exhibit good signal-to-noise ratios, with the band of positive droplets (filled rectangle) well resolved from the band of negative droplets (empty rectangle). However, when the same target is tested in a five-plex assay with only the corresponding template present, the signal-to-noise ratio becomes much less favorable. When tested in a multiplex assay, it is difficult to separate the positive droplets (signal) from the negative droplets (noise) in three of the five multiplex assays (templates 1, 2, and 4), making accurate quantification difficult or impossible. Multiplexing may cause high background because components of different assays can interact with each other to raise the noise beyond what would be expected from standard additive noise from each assay.

FIG. 17 shows data collected from droplets, generally as in FIG. 16, from a set of five singleplex assays each for a different target, a five-plex assay for five targets, and various 4-plex assays for four targets. Template is present in only one of the conditions for the various assays represented in the top plot ("P+T+"), and template is present in a subset of conditions in the bottom plot (i.e., the HEX channel control). Positive and negative bands of droplets are identified with filled and empty rectangles as in FIG. 16.

Each of the five singleplex assays (1 to 5 for different targets) exhibits a low background signal. In contrast, the background level increases dramatically when the five assays are combined as a five-plex assay. The high five-plex background is observed without polymerase or template ("P–T–"), with polymerase and without template ("P+T–"), and with polymerase and template ("P+T+"). Removing the primers and probe for each of the five assays individually from the five-plex assay to create five different four-plex assays, each missing one of the assays, shows that each of the assays contributes to the high background level.

The additive noise of the 5 singleplex assays is 2598.6, whereas the observed noise of the five-plex assay is 6863.0. Combining these assays creates an additional 4264.4 of noise, which more than doubles the noise in the system over additive noise.

FIG. 18 shows possible configurations of probe 52 in an ideal singleplex assay and a non-ideal singleplex or multiplex assay. The probe may have a smaller average spacing between photoluminophore 60 and quencher 62 in the ideal singleplex assay relative to the non-ideal singleplex or multiplex assay. For example, a primer 260 in assay may have a tendency to bind the probe, which may increase the rigidity of the probe, to keep photoluminophore 60 and quencher 62 farther apart. The greater the number of targets being quantified, the greater the chance that a probe from one assay will be bound by a component of another assay. Detection may be performed at a temperature much lower than the temperatures used for amplification, such as at room temperature, thereby allowing a mismatched reporter 262 to form. Accordingly, an exemplary theory behind the greater than additive noise observed is that components from the different assays interact with each other to increase probe rigidity, which reduces quenching and drives up the noise.

Example 10. Test of a Sink that Promotes Intermolecular Quenching

Figure 19:
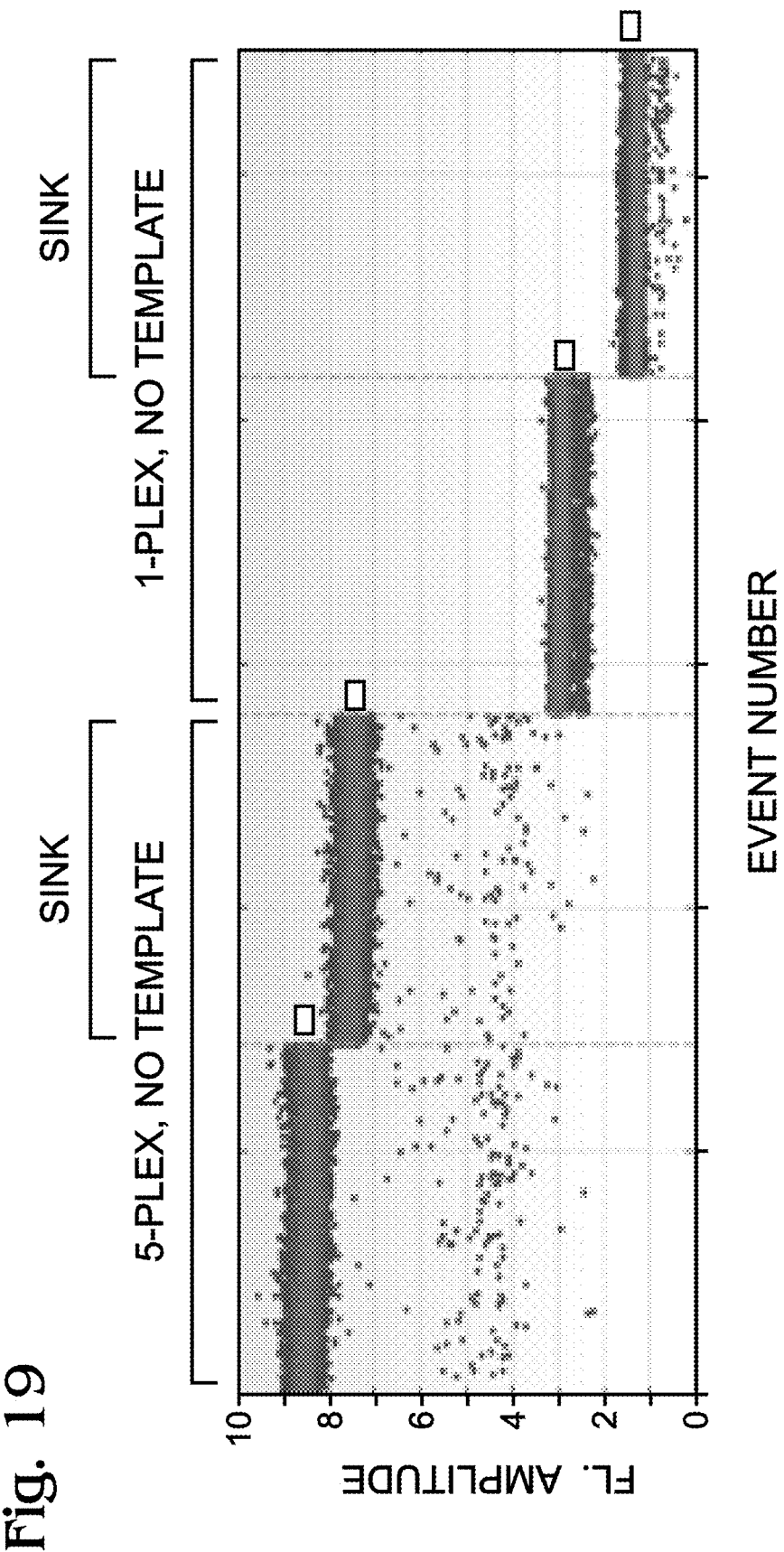
FIG. 19 is a plot of fluorescence amplitude measured for a series of assays performed in droplets with five probes or one probe, respectively, in the absence and presence of a sink designed to position copies of one of the probes adjacent one another such that a photoluminophore of one probe copy is quenched by a quencher of another probe copy, in accordance with aspects of the present disclosure.

This example describes exemplary data collected from droplets formed to contain a reporter according to Example 5 (FIG. 11); see FIG. 19.

The plot of FIG. 19 shows data collected from droplets each containing either a five-plex assay as in FIGS. 16 and 17 or a singleplex assay. No template was added, so each band on the plot represents negative droplets, as indicated by an unfilled rectangle to the right of each band. In the multiplex assay, each of the assays targets a different gene. The primer and probe concentrations for each assay were 900 nM and 250 nM, respectively. A sink was included in the droplets at a concentration of 500 nM, where indicated. The sink was designed as in FIG. 11 and binds the probe for only one target assay. Use of the sink decreases the fluorescence of the negative droplets in both the singleplex assay and the multiplex assay (even though the sink binds to only one of the five probes used in the multiplex assay). Accordingly, the sink can reduce the amplitude of negative droplets (noise) in multiplex and singleplex droplet PCR analysis. Addition of sinks that bind to others of the five probes can reduce background further.

Example 11. Comparison of Different Probes in Droplet-Based Assays

Figure 20:
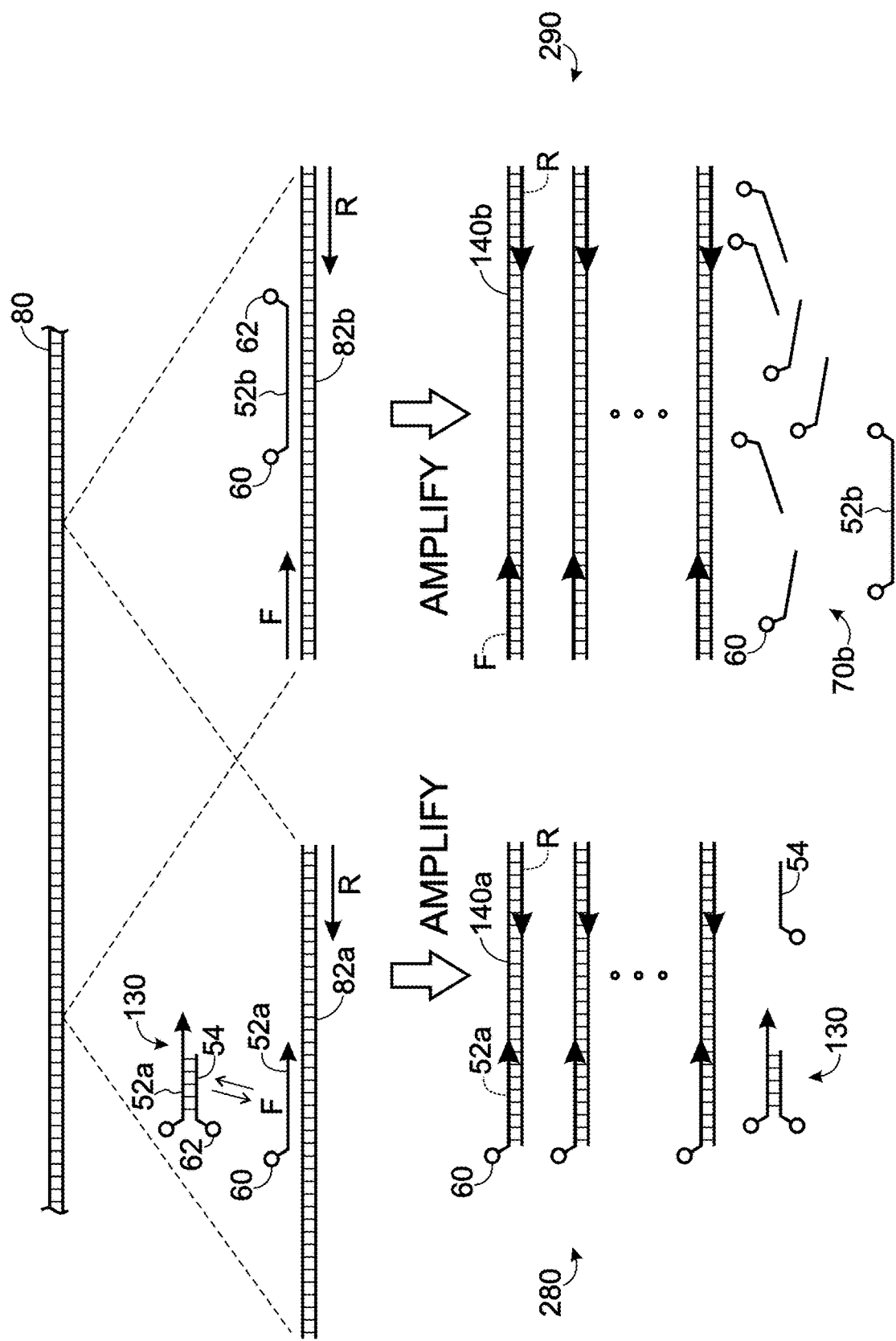
FIG. 20 is a schematic flowchart illustrating a pair of distinct strategies for assay of overlapping target sequences in partitions (e.g., droplets), with the strategy on the left utilizing a probe acting as a primer and bound by a sink at room temperature, and the strategy on the right utilizing a self-quenched probe positioned intermediate a pair of primers, in accordance with aspects of the present disclosure.
Figure 21:
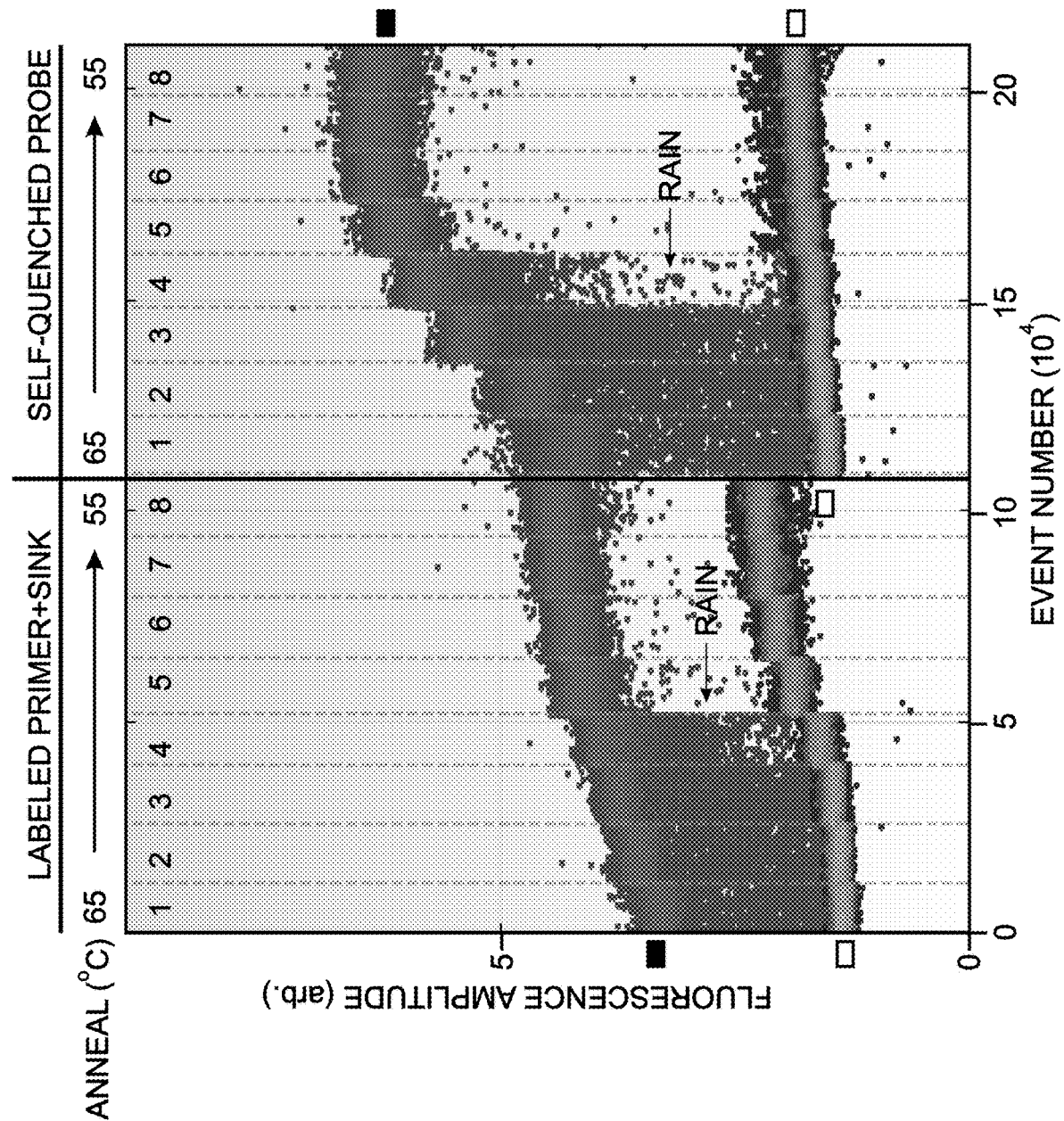
FIG. 21 is a plot of fluorescence data collected from droplets and comparing the two strategies of FIG. 19 at different annealing temperatures for thermocycling the droplets, in accordance with aspects of the present disclosure.
Figure 22:
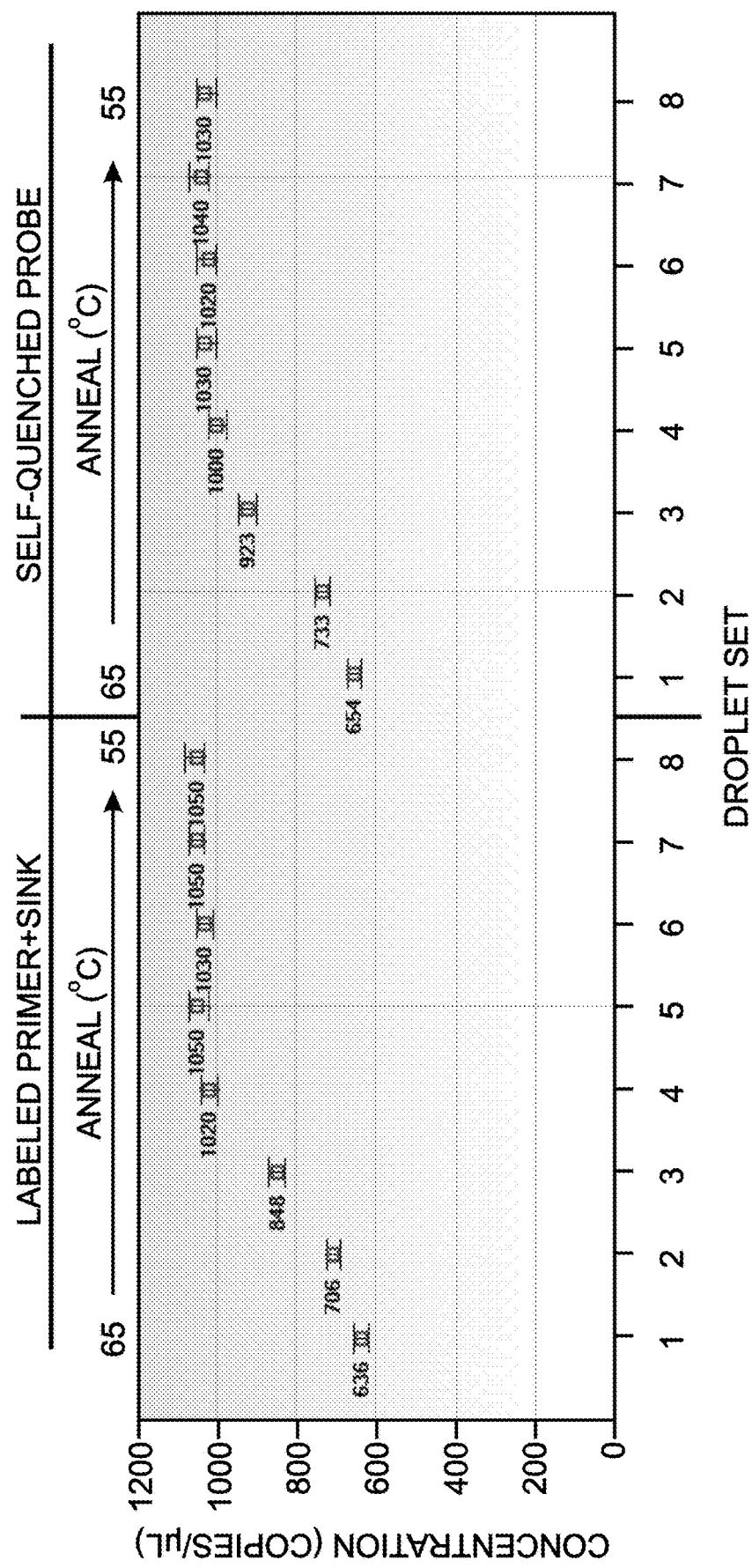
FIG. 22 is a graph of target concentration determined from the data of FIG. 21 for each of the sets of droplets of each assay strategy, in accordance with aspects of the present disclosure.

This example compares distinct strategies for assay of a target region in droplets; see FIGS. 20-22.

FIG. 20 shows a schematic flowchart illustrating a pair of distinct strategies for assay of respective, overlapping target regions 82a and 82b in partitions (e.g., droplets).

The strategy on the left, strategy 280, involves a labeled primer (probe 52a) and a sink 54. Strategy 280 can quantify target region 82a of template 80 and utilizes probe 52a acting as a forward primer to generate labeled amplicon 140a that is not quenched. The unused probe that is not incorporated can be bound by sink 54 to form quenched reporter 130 at the detection temperature.

The strategy on the right, strategy 290, involves a self-quenched probe 52b that is not an amplification primer. The probe may, for example, be a Taqman® probe. Strategy 290 can quantify target region 82b of template 80 and utilizes probe 52b that binds intermediate a pair of amplification primers (F and R). The amplification primers define an amplicon that encompasses the amplicon of strategy 280. Probe 52b is cleaved during amplification to form a degraded probe 70b that is not quenched by quencher 62. Residual, unused probe also may be present, particularly in target-negative partitions.

Fragmentation of DNA can artificially reduce concentration measurements when using PCR-based methods. Many sources of DNA such as FFPE (formalin-fixed paraffin-embedded) or environmental samples are highly fragmented. One possible approach to alleviate the errors caused by fragmentation is to create assays that are as short as possible. Strategy 280 has advantages over strategy 290 in this regard. For example, use of a probe that serves as an amplification primer allows the forward and reverse primers to be positioned more closely to one another than when the probe binds intermediate the pair of amplification primers. Accordingly, a shorter target region (e.g., less than about 75, 60, or 50 nucleotides) can be quantified with the strategy on the left, which reduces the number of target copies that are missed due to random breakage during isolation/preparation of nucleic acid that provides the target.

FIG. 21 shows a plot of fluorescence data collected from sets of droplets assayed according to strategy 280 ("labeled primer+sink") or strategy 290 ("self-quenched probe") of FIG. 20, with primers for a CCND1 target. The oligonucleotides used for strategy 280 are as follows: 5'-FAM-TATCT-GAGGGGCGGGAGAG-3', probe/forward primer (SEQ ID NO:1); 5'-GAGGTCACGACATTTTAGCG-3', reverse primer (SEQ ID NO:2); and 5'-CGCCCCTCAGATA-IB-3', sink, where IB is Iowa Black® dark quencher (SEQ ID NO:3). The primers used for strategy 290 are as follows: 5'-ACATTGATTCAGCCTGTTTGG-3', forward primer (SEQ ID NO:4); 5'-GAATTCATCGGAACCGAACTT-3', reverse primer (SEQ ID NO:5); and 5'-FAM-TCCTTGCACCCATGCCTGTCCA-IB-3', probe (SEQ ID NO:6).

Eight sets of droplets (identified with the numbers 1-8) were processed according to each strategy, with amplification promoted by thermocycling at a distinct annealing temperature for each set of droplets. More particularly, set 1 was an annealed at 65° C., set 8 at 55° C., and sets 2-7 at temperature increments between the annealing temperatures of sets 1 and 8. The droplets in each set were passed through a detector serially and were detected as individual "events" based on a fluorescence amplitude measured from each droplet. The detected droplets or "events" are numbered in sequence on the graph and are plotted as individual points. Target-negative droplets of the set produce a lower fluorescence amplitude, identified by an unfilled rectangle, and target-positive droplets of the set produce a higher fluorescence amplitude, identified by a filled rectangle. The presence of droplets having an intermediate fluorescence amplitude ("rain") is reduced substantially by decreasing the annealing temperature, as seen in sets 5-8 for each strategy.

FIG. 22 shows a graph of target concentrations determined from the data of FIG. 21, for each set of droplets. Sets 5-8 for each assay strategy generated substantially the same target concentration. The experiments presented in this example show that an AMP assay with a sink produced an equivalent concentration measurement to a TaqMan® assay for the same gene, CCND1. The AMP assay does not require space for an additional probe and can amplify a significantly shorter product than a TaqMan® assay. Furthermore, AMP assays take advantage of contact quenching and are easily amenable to multiplexing.

Example 12. Test of a Sink that Binds a Pair of Self-Quenched Probes

This example describes exemplary data collected from droplets formed to contain self-quenched probes 52a and 52b that are specific, respectively, for a wild type target 82a and a mutant target 82b. Each of probes 52a and 52b may be bound by the same sink 54 at a detection temperature to form respective quenched reporters 130a and 130b. The assay strategy is generally as described in Section I (e.g., see FIGS. 1-3) and elsewhere in the present disclosure; see FIGS. 23 and 24.

Figure 23:
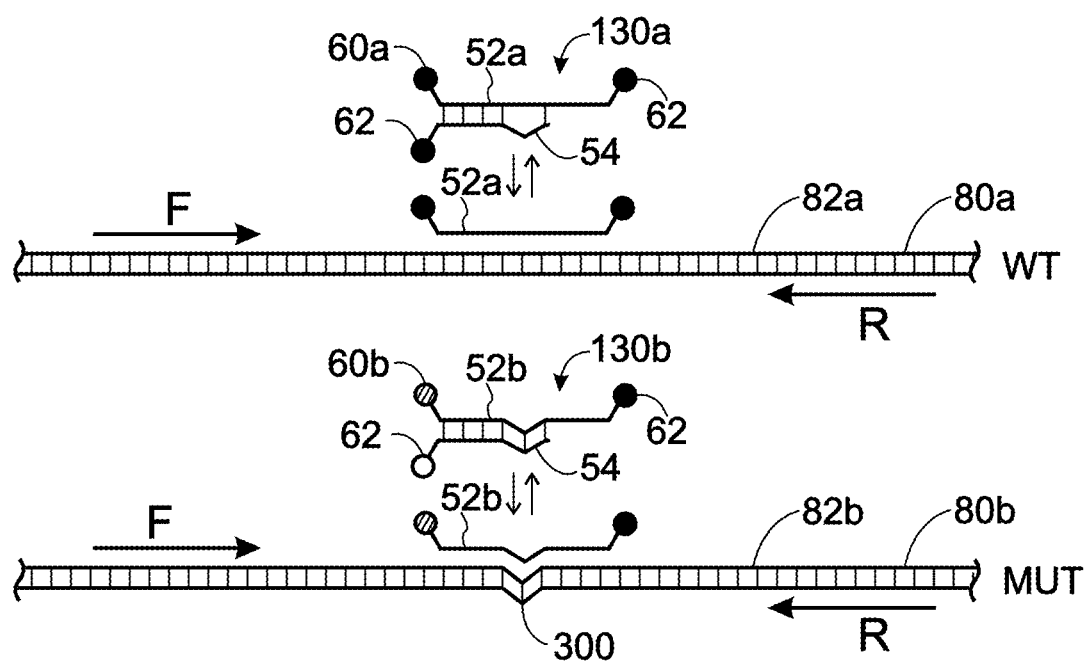
FIG. 23 is a schematic of a strategy for performing a multiplex assay of wild-type and mutant alleles of a K-Ras target in droplets, with probes, amplification primers, and a sink aligned with their prospective binding sites in wild-type (WT) and mutant (MUT) templates, in accordance with aspects of the present disclosure.
Figure 24:
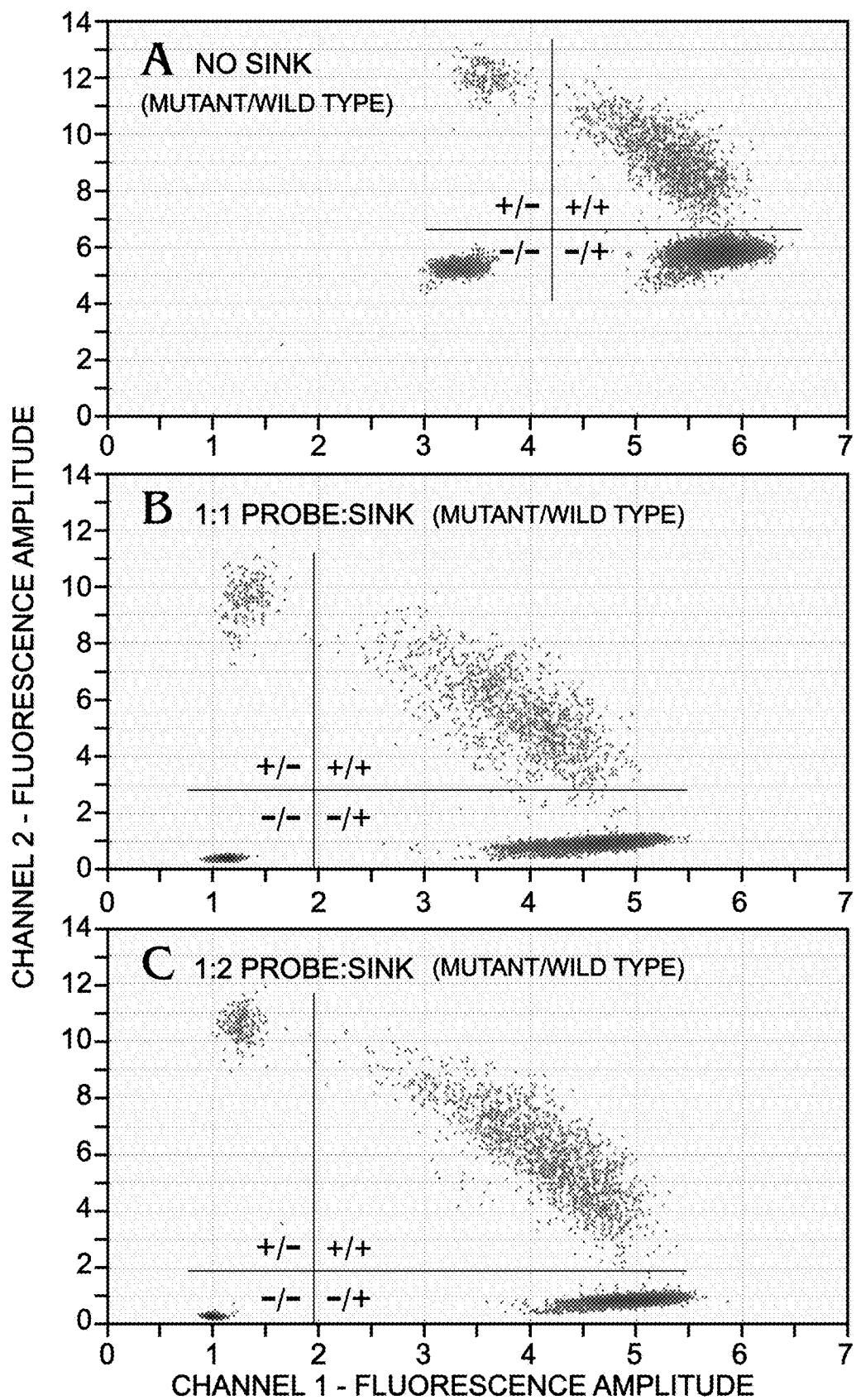
FIG. 24 is a series of scatter plots of fluorescence data collected from a multiplex assay of a K-Ras target performed in droplets according to the strategy of FIG. 23, with different amounts of the sink present in the droplets, in accordance with aspects of the present disclosure.

FIG. 23 shows a schematic of a strategy for performing a multiplex assay (A146T assay) of wild-type and mutant alleles of a K-Ras gene in droplets. Probes 52a and 52b and primers (F and R) are aligned with their prospective binding sites in wild-type and mutant templates 80a and 80b. Targets 82a and 82b may differ at a single nucleotide (or more than one nucleotide), identified at 300 in the mutant template.

Droplets were formed with one pair of primers for amplification of the same region of K-Ras from wild-type and mutant templates. The sequences of the primers are as follows: 5'-AGAAGCAATGCCCTCTCAAG-3', forward primer (SEQ ID NO:7); and 5'-AAACAGGCTCAGGACT-TAGC-3', reverse primer (SEQ ID NO:8). The assay used a wild-type probe 52a and a mutant probe 52b labeled with distinct fluorophores, namely, HEX dye (60a) and FAM dye (60b), respectively, and each conjugated to the same quencher, IOWA BLACK® dark quencher ("IB"). The respective sequences of probes 52a and 52b are as follows: 5'-HEX-ATTGAAACATCAGCAAAGACAAGACA-IB-3' (SEQ ID NO:9); and 5'-FAM-TTGAAACATCAACAAA-GACAAGACAGG-IB-3' (SEQ ID NO:10). The probes have a single nucleotide difference that allows the probes to selectively bind to wild-type or mutant template/amplicon. Different sets of droplets were formed to contain either no sink 54 or the sink at two different ratios of probe to sink (1:1 and 1:2). The sink is perfectly complementary to the mutant probe (no mismatches). However, the sink binds substantially to both probes at the detection temperature used (room temperature), and thus is not selective for the mutant probe. The sequence of the sink is 5'-GTTGATGTTTCAA-IB-3' (SEQ ID NO:11).

FIGS. 24A-C show scatter plots of fluorescence data collected from droplets formed without a sink (A) and with different amounts of the sink (B and C). Each droplet produces a point in the plot, with the position of the point determined by the channel 1 fluorescence amplitude (HEX dye, wild-type probe) of the droplet on the X-axis and the channel 2 fluorescence amplitude (FAM dye, mutant probe) of the same droplet on the Y-axis. The droplets form four clusters or populations, which are color-coded and located in four quadrants: black (−/−) for double negative (neither target present), blue (+/−) for single positive with only the mutant target present, green (−/+) for single positive with only the wild-type target present, and brown (+/+) for double positive (mutant and wild-type targets present). In FIG. 24A, without a sink, the basal fluorescence of negative droplets is relatively high—the fluorescence amplitude difference between negative and positive droplets for each target is only about two-fold. In FIGS. 24B and 24C, the sink produces a substantial decrease in the background fluorescence of droplets negative for either or both targets. The sink produces a relatively insubstantial reduction in the fluorescence amplitude of droplets positive for either or both targets.

Example 13. Test of a Sink for a Probe Containing No Quencher

This example describes exemplary data collected from droplets formed to contain a probe and a sink and then processed to promote amplification, generally according to Example 2 (e.g., see FIG. 8); see FIGS. 25 and 26.

FIG. 25 shows a schematic of another strategy for performing a multiplex assay (A146T assay) of wild-type and mutant alleles of a K-Ras gene in droplets. The strategy is substantially the same as in FIG. 23, except that each probe 52a and 52b is labeled with a photoluminophore but not a quencher. The sequences of probes 52a and 52b are 5'-HEX-ATTGAAACATCAGCAAAGACAAGACA-3' (SEQ ID NO:12) and 5'-FAM-TTGAAACATCAACAAAGACAAGACAGG-3' (SEQ ID NO:13). The sink (SEQ ID NO:11) of the preceding example was used here, too.

FIG. 26 present fluorescence data collected from droplets formed according to the strategy of FIG. 25. The data is plotted as described above for FIG. 24 and shows that intermolecular quenching of probes with a sink, without probe self-quenching, resolves target populations into distinct clusters.

Example 14. Allele-Specific Amplification

Figure 27:
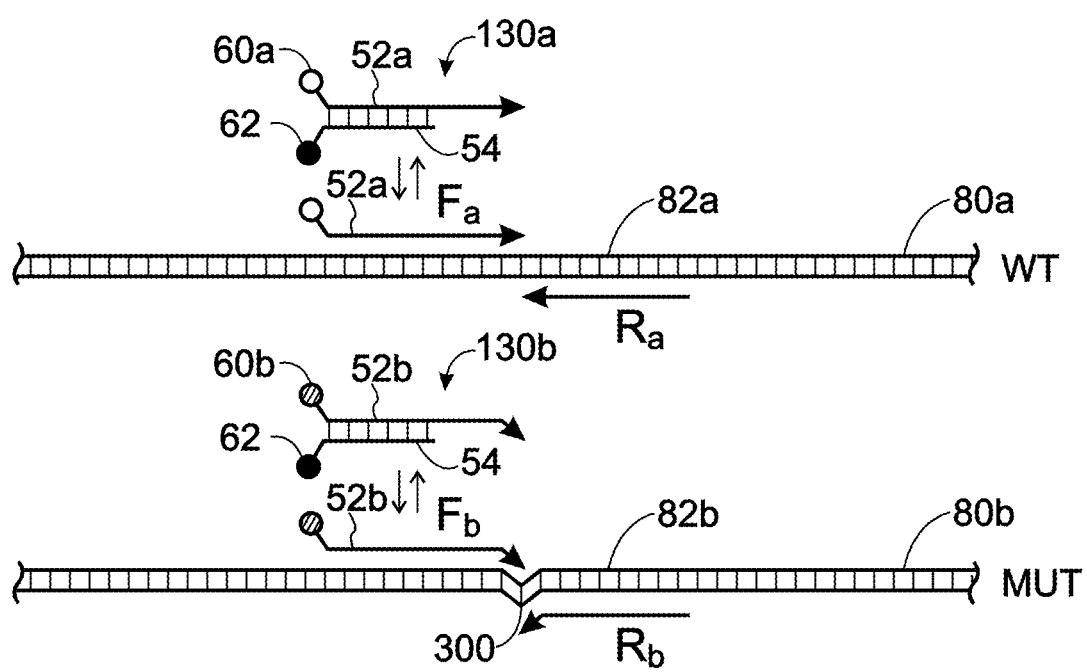
FIG. 27 is a schematic of a strategy for performing a duplex, allele-specific assay of target sequences, in accordance with aspects of the present disclosure.

This example describes an exemplary strategy for allele-specific amplification in the presence of a sink that binds allele-specific probes that function as primers; see FIG. 27.

FIG. 27 shows a schematic of a partition-based strategy for performing a duplex assay of wild-type and mutant alleles of a gene. The alleles may differ by any suitable number of nucleotides, such as a single nucleotide polymorphism 300, as shown here. A wild-type target 82a may be amplified from a wild-type template 80a with a first pair of primers, namely, a forward primer (Fa) (probe 52a) and a reverse primer (Ra), that each prime specifically on the wild-type template relative to the mutant template. A mutant target 82b may be amplified from a mutant template 80b with a different pair of primers, namely, a forward primer (Fb) (probe 52b) and a reverse primer (Rb), that each prime specifically on the mutant template relative to the wild-type template. Each forward primer and each reverse primer may end on the variant nucleotide position as shown, such that the primers overlap by at least one nucleotide. Probes 52a and 52b may be labeled with respective photoluminophores 60a and 60b that are optically distinguishable. The probes may be quenched intermolecularly at room temperature, as reporters 130a and 130b, by binding to copies of the same sink 54, which is complementary to each probe. In other embodiments, either allele may be quantified in a singleplex assay.

In other embodiments, unlabeled primers may be used for allele-specific amplification, and a generic reporter (e.g., an intercalating dye) may be used to label one or more amplicons produced by amplification of one or both targets. Both targets may be assayed together in a multiplex assay by adjusting one or more primer concentrations and/or primer melting temperatures to render the signal amplitude of partitions positive for one of the targets distinguishable from the signal amplitude of partitions positive for the other target (and, optionally, distinguishable from the signal amplitude of partitions positive for both targets).

Example 15. Probe Displacement Assays without Probe Degradation

This example describes an exemplary strategy for a target assay in which probe is displaced but not degraded as primer is incorporated into amplicon; see FIGS. 28-31.

Figure 28:
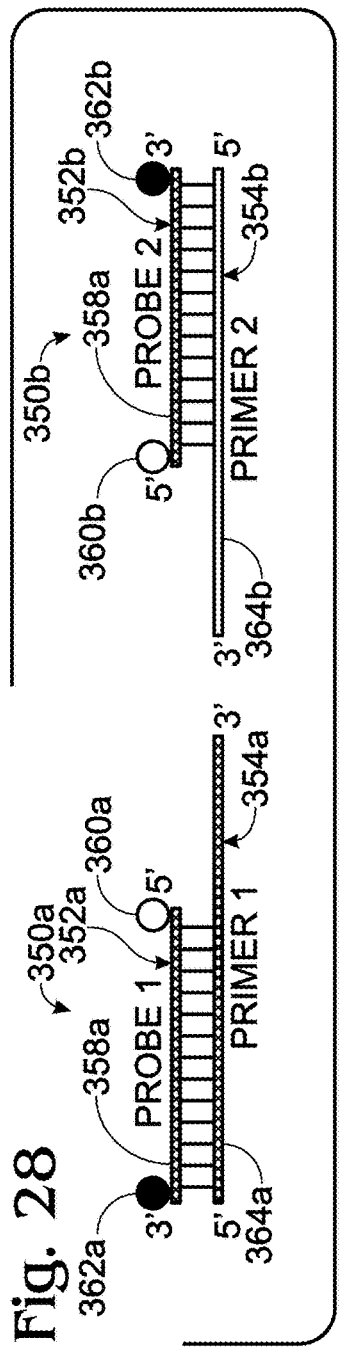
FIG. 28 is a schematic view of a pair of exemplary reporters each composed of base-pairing oligomers (a "probe" and a "primer") that collectively provide a photoluminophore and an energy transfer partner, such as a quencher, for the photoluminophore, in accordance with aspects of the present disclosure.

FIG. 28 shows exemplary reporters 350a,b used in the assay. The reporters each include a probe 352a,b and a primer 354a,b. The probes, in turn, each include at least a probe oligomer 358a,b, one or more luminophores 360a,b, and one or more quenchers 362a,b. The primers, in turn, each include at least a primer oligomer 364a,b. The probe oligomer and the primer oligomer for each reporter may be partially or fully complementary and are capable of base-pairing with one another below a melting temperature of the reporter. The luminophore(s) and quencher(s) are positioned on each probe such that the probe is more luminescent (i.e., produces more photoluminescence) when the probe is bound to the respective primer than when the probe is unbound. Specifically, when the probe is bound to the primer, the luminophore(s) and quencher(s) are held apart, reducing the effect of the quencher on luminescence of the luminophore. In contrast, when the probe is unbound, either because the system is above the melting point of the probe and primer pair, or because at least some primer is unavailable to bind probe because the primer has been incorporated into amplicon during amplification, the luminophore and quencher are not held apart (although still bound to the same oligonucleotide) and may come into sufficient proximity that the quencher reduces or eliminates luminescence from the luminophore. Luminophore and quencher may be positioned, in any suitable number each, at any suitable positions on the probe capable of yielding the effect described above.

Figure 29:
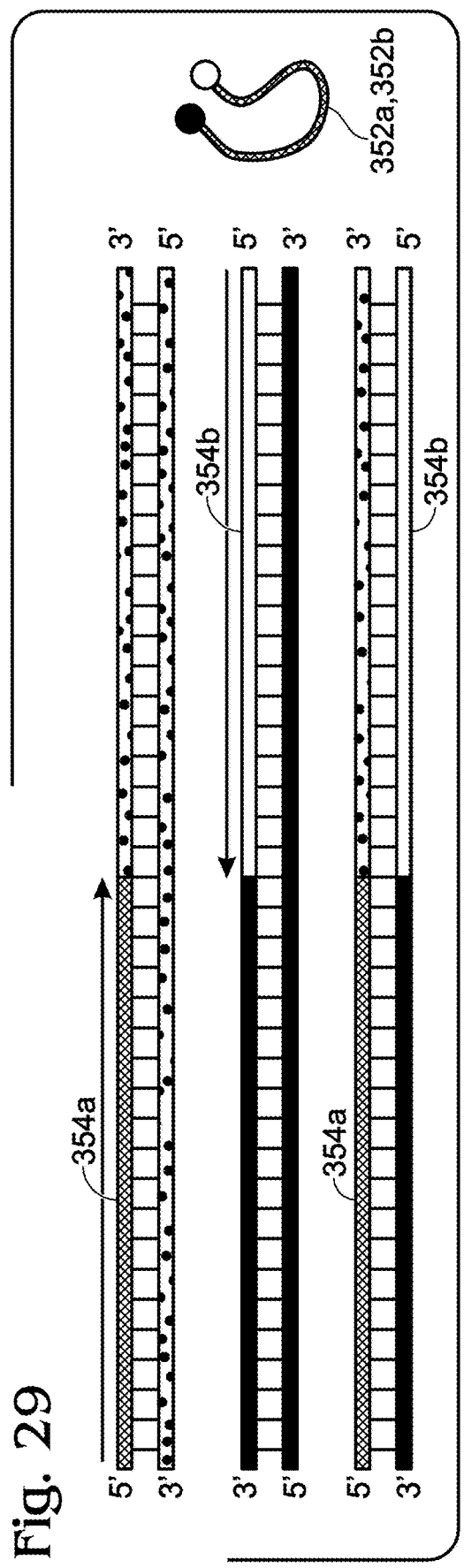
FIG. 29 is a schematic view of exemplary configurations produced by amplification of target in the presence of the reporters of FIG. 28, in accordance with aspects of the present disclosure.

FIGS. 28 and 29 show exemplary configurations produced by amplification. Fluorescence typically is detected at the completion of the amplification reaction and, for droplet-based assays, in a sample that has been partitioned into droplets before amplification. FIG. 28 shows configurations produced in the absence of target, such as target DNA or target RNA. Here, the probe remains duplexed with the primer such that the associated luminophore and quencher are fixed at a distance from one another, leading to higher fluorescence. In a droplet assay, these configurations would correspond to no-target droplets or no DNA/no RNA control droplets. FIG. 29, in contrast, shows configurations produced in the presence of target. Here, primer has been incorporated into amplicons, leaving excess probe free-floating and self-quenching. In other words, in samples, such as droplets, that have target DNA or target RNA, probe will be displaced from primer as primer becomes a part of the (PCR-) amplified product. Once the probe is displaced from the primer, the quencher and luminophore will be free to interact directly with one another, allowing the quencher to quench the fluorescence of the luminophore and reduce fluorescence. Thus, positive signal (i.e., signal from samples positive for target, in which amplification occurred) will be lower than negative signal (i.e., signal from samples negative for target, in which amplification did not occur). Total assay signal, including both positive signal and negative signal, can be increased by using the same fluorophore for both primer-probe pairs (e.g., for forward and reverse primers). Conversely, total assay signal can be decreased by omitting fluorophore (or both fluorophore and quencher) from one of the primer-probe pairs.

Figure 30A:
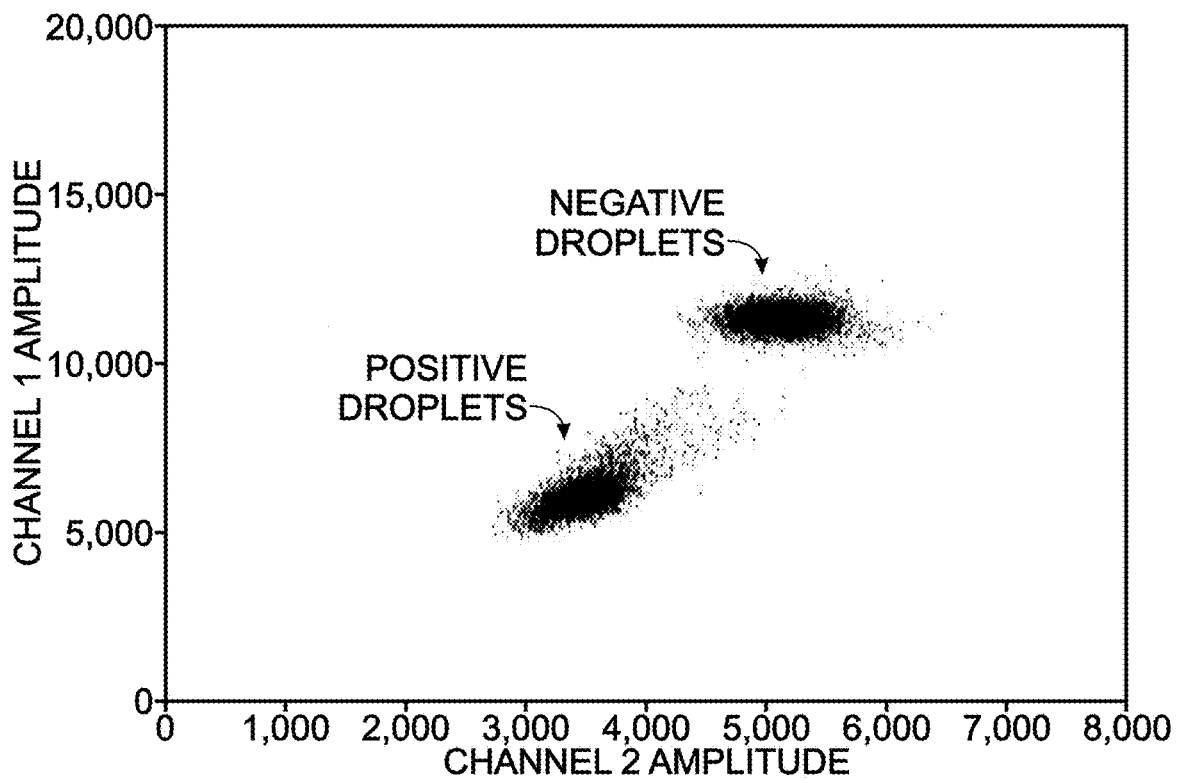
FIGS. 30A and 30B are a pair of scatter plots of fluorescence data collected from a multiplex assay using two reporters, such as the reporters of FIG. 28, one reporter having a probe labeled with a FAM fluorophore and the other reporter having a probe labeled with a HEX reporter.
Figure 30B:
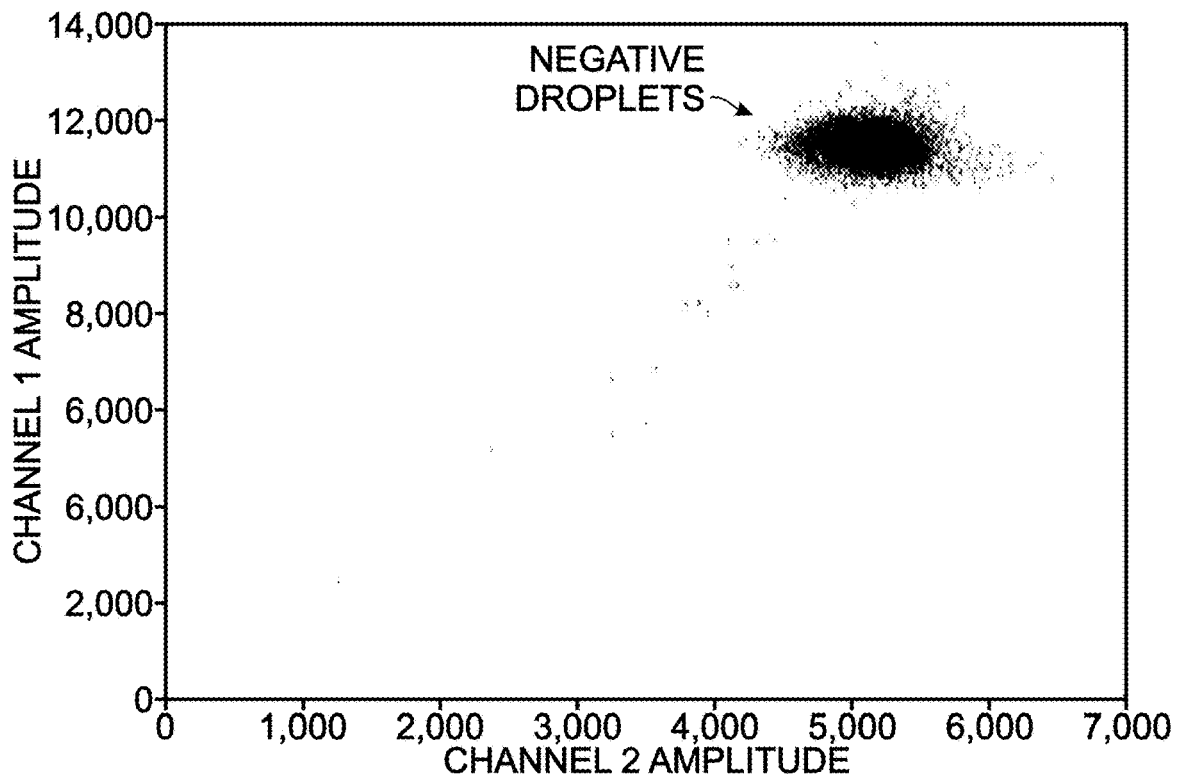

FIG. 30 shows representative data, plotted in two dimensions, from an assay such as the assay of FIGS. 28 and 29 obtained using a FAM-labeled probe partially complementary to one primer and a HEX-labeled probe partially complementary to the other primer. Panel A shows results from a sample containing target DNA. The results include data clusters from partitions both negative for ("negative cluster") and positive for ("positive cluster") the target DNA. The fluorescence of the negative cluster (in which probe and primer remain bound) is higher than the fluorescence of the positive cluster (in which probe is unbound or free in solution). Panel B shows results from a control well not containing DNA. The negative sample or no-target sample has only the higher fluorescent cluster of droplets.

Figure 31:
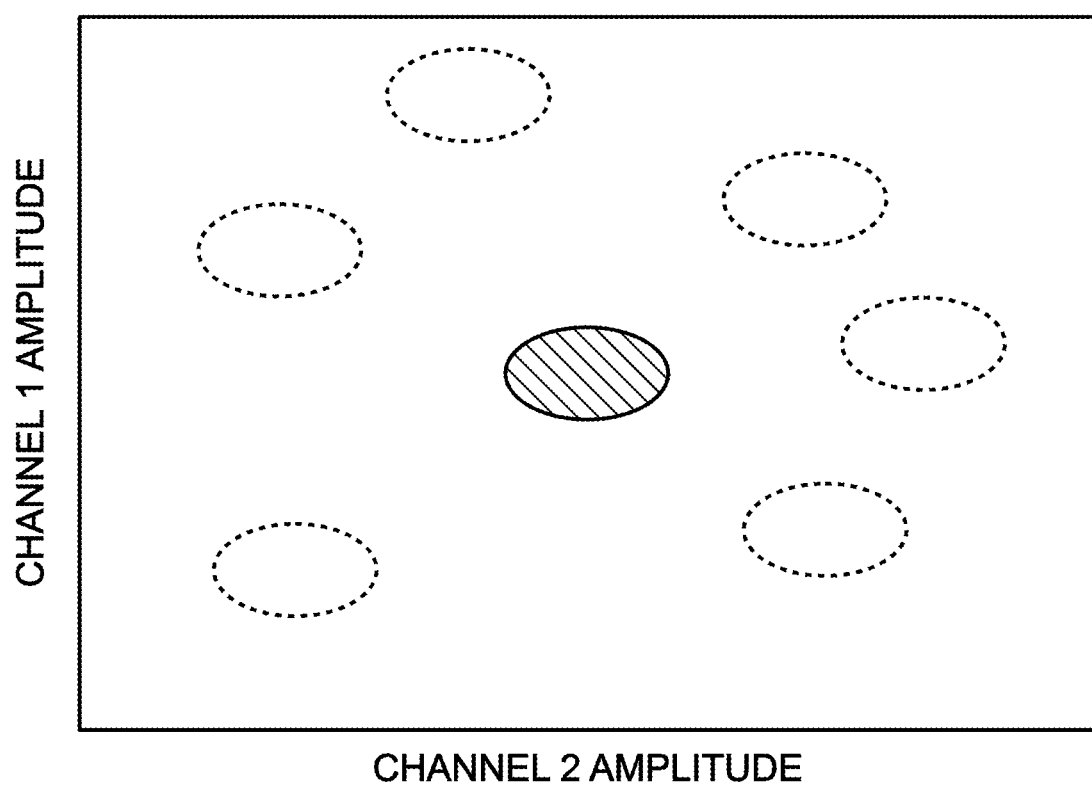
FIG. 31 is a schematic scatter plot of fluorescence data illustrating how the reporters of FIG. 28 may be used to design multiplex assays by allowing signal (open clusters) from the positive droplets to occupy a space in 360 degrees around the signal (shaded cluster) for negative sample.

FIG. 31 illustrates how displacement probe assays may be used in combination with traditional TaqMan® assays to create a space for the positives 360 degrees around the central negative cluster. The signal shift may be achieved through mixing different fluorophores or dyes on each probe as well as assay types. In other words, signal may be purposely altered by adding a weak or strong quencher and/or mixed by using one fluorophore for one primer-probe pair and a different fluorophore for the other primer-probe-pair. This, in turn, should increase multiplexing.

The assays described in this example may have several advantages. First, because probe and primer bind to one another, allowing probe and primer to utilize the same sequence space, the probes may be used for the detection of nucleic acids that are too short for a traditional TaqMan® assay (FIG. 28). Second, the method provides the potential to multiplex by allowing for the positive droplets to occupy a space in 360 degrees around the negative signal (FIG. 31). These probe displacement assays may be used for any suitable application; however, they are especially useful for (1) detection of targets that are only long enough for a primer to be used on each side which is approximately 15-40 nucleotides long, (2) increasing the number of amplifiable copies of DNA or RNA in a fragmented or damaged sample, and (3) micro RNAs that are 15-25 nucleotides long.

The assays in this example (and other examples) may be modified by replacing fluorescence quencher with a fluorescence enhancer, such as an antenna that transfers energy to, rather than siphoning energy from, the fluorophore. (This may be accomplished, for example, by using a donor and acceptor pair, then exciting both donor and acceptor, and finally detecting acceptor fluorescence.) This would have the effect, in this example, of reversing the relative intensities of the positive and negative signals, because amplification leading to unbound probe would bring fluorophore and enhancer in proximity, increasing rather than decreasing fluorescence.

Example 16. Selected Embodiments I

This example describes selected embodiments of assay methods and compositions, presented as a series of indexed paragraphs.

1. A method of performing an assay, the method comprising: (A) providing partitions including a target at partial occupancy, a probe including a photoluminophore, and a sink that binds the probe to reduce an ability of the photoluminophore to emit light; (B) amplifying the target in the partitions; (C) detecting light that is dependent at least in part on a presence of the photoluminophore in the partitions; and (D) determining a level of the target present in the partitions based on the light detected.

2. The method of paragraph 1, wherein the step of amplifying is performed with one or more primers, and wherein the probe acts as one of the one or more primers for the step of amplifying.

3. The method of paragraph 2, wherein the step of amplifying is performed with a first primer and a second primer that define opposite ends of an amplicon produced by the step of amplifying, wherein the probe is the first primer, and wherein the second primer is conjugated to a quencher for the photoluminophore.

4. The method of paragraph 3, wherein the sink includes an oligonucleotide that is complementary to the first primer.

5. The method of paragraph 4, wherein the oligonucleotide is conjugated to a quencher for the photoluminophore.

6. The method of any of paragraphs 1 to 5, wherein the step of providing partitions includes a step of providing partitions containing a pair of probes, wherein the step of amplifying is performed with the pair of probes each including a distinct photoluminophore and acting as a primer for a distinct target, and wherein the step of determining includes a step of determining a level of each of the distinct targets.

7. The method of paragraph 1, wherein the probe is a first probe including a first photoluminophore, further comprising a second probe including a distinct second photoluminophore and configured to bind to the target at a different position than the first probe.

8. The method of paragraph 7, wherein the second probe is not bound by the sink.

9. The method of paragraph 8, wherein the second probe is conjugated to a quencher.

10. The method of any of paragraphs 7 to 9, wherein the second probe is a primer that is extended during the step of amplifying.

11. The method of paragraph 10, wherein each of the first probe and the second probe is a distinct primer that is extended during the step of amplifying.

12. The method of any of paragraphs 7 to 11, wherein the step of determining a level of the target is based on light detected from the first photoluminophore of the first probe and the second photoluminophore of the second probe.

13. The method of paragraph 7, wherein only one of the first probe and the second probe is a primer that is extended during the step of amplifying.

14. The method of paragraph 13, wherein neither the first probe nor the second probe is a primer that is extended during the step of amplifying.

15. The method of any of paragraphs 1 to 14, wherein the partitions are droplets.

16. The method of any of paragraphs 1 or 15, wherein the probe includes a probe oligonucleotide, wherein the sink includes a sink oligonucleotide, and wherein the probe oligonucleotide is longer than the sink oligonucleotide and/or is configured to form a greater number of base pairs with the target than with the sink oligonucleotide.

17. The method of any of paragraphs 1 to 16, wherein a plurality of the partitions contain no copies of a template corresponding to the target.

18. The method of any of paragraphs 1 to 17, wherein a plurality of the partitions contain only one copy of a double-stranded or single-stranded template corresponding to the target.

19. The method of any of paragraphs 1 to 18, wherein the step of providing partitions includes a step of providing partitions in which the target is formed by a pair of complementary strands.

20. The method of any of paragraphs 1 to 19, wherein the sink includes an oligonucleotide, and wherein the oligonucleotide binds specifically to the probe.

21. The method of any of paragraphs 1 to 20, wherein the sink includes a quencher for the photoluminophore.

22. The method of paragraph 21 wherein the quencher is not substantially photoluminescent.

23. The method of paragraph 21, wherein the quencher is photoluminescent, and wherein the step of detecting light includes a step of detecting light emitted by the quencher.

24. The method of any of paragraphs 20 to 23, wherein the quencher is conjugated to a 3'-end of the oligonucleotide.

25. The method of any of paragraphs 20 to 23, wherein the quencher is at an internal position between the 5'-end and the 3'-end of the oligonucleotide.

26. The method of any of paragraphs 1 to 25, wherein at least two distinct targets are amplified in the partitions, wherein one or more of the partitions contain each of the targets, and wherein a level of each target is determined.

27. The method of any of paragraphs 1 to 26, wherein the sink does not include a quencher for the photoluminophore.

28. The method of any of paragraphs 1 to 27 wherein the photoluminophore is a fluorophore, and wherein the step of detecting light includes a step of detecting fluorescence of the fluorophore.

29. The method of any of paragraphs 1 to 28, wherein the probe is capable of specifically binding a region of the target.

30. The method of any of paragraphs 1 to 29, wherein the probe includes an oligonucleotide, and wherein the quencher and the photoluminophore are connected to respective opposite ends of the oligonucleotide.

31. The method of any of paragraphs 1 to 30, wherein the step of providing partitions includes a step of providing partitions surrounded by a continuous liquid phase.

32. The method of paragraph 31, wherein the continuous liquid phase is immiscible with the partitions.

33. The method of paragraph 31 or 32, wherein the continuous liquid phase is composed at least predominantly of oil.

34. The method of any of paragraphs 1 to 33, wherein the step of providing partitions includes a step of providing partitions in which the sink is present at a higher concentration than the probe.

35. The method of any of paragraphs 1 to 34, wherein the sink is configured to promote intramolecular quenching of the probe.

36. The method of paragraph 35, wherein a single copy of the sink is configured to circularize a single copy of the probe.

37. The method of paragraph 35, wherein a single copy of the sink is configured to bind two copies of the probe, and wherein a single copy of the probe is configured to bind two copies of the sink.

38. The method of any of paragraphs 1 to 37, wherein the step of providing partitions includes a step of providing partitions containing more copies of the sink than the probe.

39. The method of any of paragraphs 1 to 38, wherein the step of providing partitions includes a step of providing partitions containing an amount of the sink sufficient to bind substantially all of the probe in each partition.

40. The method of any of paragraphs 1 to 39, wherein the step of amplifying includes a step of thermally cycling the partitions.

41. The method of paragraph 40, wherein the step of amplifying includes a step of performing a polymerase chain reaction.

42. The method of any of paragraphs 1 to 41, wherein the step of amplifying includes a step of generating an amplicon corresponding to the target, and wherein the probe binds to a region of the amplicon.

43. The method of any of paragraphs 1 to 42, wherein the step of detecting light is performed after amplification of the target has reached an endpoint.

44. The method of any of paragraphs 1 to 43, wherein light detected is emitted at least in part by the photoluminophore.

45. The method of any of paragraphs 1 to 43, wherein light detected is emitted at least in part by an energy transfer partner of the photoluminophore 46. The method of any of paragraphs 1 to 45, further comprising a step of irradiating the partitions with light that excites the photoluminophore 47. The method of any of paragraphs 1 to 46, further comprising a step of determining a fraction of partitions that are positive or that are negative for amplification of the target, and wherein the step of determining a level is based on the fraction.

48. The method of any of paragraphs 1 to 47, wherein the step of determining a level includes a step of determining a concentration of the target.

49. The method of any of paragraphs 1 to 48, wherein the sink binds to the probe to form a reporter having a melting temperature, and wherein the step of amplifying is performed with the partitions maintained above the melting temperature of the reporter.

50. The method of paragraph 49, wherein the melting temperature is less than 50 degrees Celsius.

51. The method of paragraph 49 or 50, wherein the step of detecting light is performed with the partitions below the melting temperature of the reporter.

52. The method of paragraph 1, wherein the partitions contain template copies for a first allele and/or a second allele of the target, wherein the step of amplifying is performed with a forward primer and a reverse primer that are each selectively extendable when bound to template for the first allele relative to template for the second allele, and wherein the probe is the forward primer or the reverse primer.

53. The method of paragraph 52, wherein the forward primer and the reverse primer overlap by at least one nucleotide.

54. The method of paragraph 52, wherein the forward primer and the reverse primer overlap at a site of nucleotide variation between the first and second alleles.

55. The method of paragraph 54, wherein each of the forward primer and the reverse primer ends at the site of nucleotide variation.

56. The method of any of paragraphs 52 to 55, wherein the sink includes a quencher for the photoluminophore.

57. The method of any of paragraphs 52 to 56, wherein the probe is a first probe, further comprising a second probe that is extendable selectively as a primer when bound to template for the second allele relative to template for the first allele.

58. The method of paragraph 57, wherein the sink binds to the second probe.

59. A method of performing an assay, the method comprising: (A) providing droplets including a target at partial occupancy, a probe having a photoluminophore and a quencher for the photoluminophore, and an oligonucleotide that binds the probe to reduce an ability of the photoluminophore to emit light; (B) amplifying the target in the droplets; (C) detecting light emitted at least in part by the photoluminophore; and (D) determining a level of the target based on the light detected.

60. A method of performing an assay, the method comprising: (A) forming a reaction mixture including a target, a probe having a photoluminophore and a quencher for the photoluminophore, and a first oligonucleotide that binds the probe to reduce an ability of the photoluminophore to emit light, wherein the probe includes a second oligonucleotide configured to bind a region of an amplicon; (B) amplifying the target to generate the amplicon; and (C) detecting light emitted at least in part by the photoluminophore.

61. The method of paragraph 60, further comprising a step of forming partitions containing portions of the reaction mixture, wherein the step of amplifying is performed in a plurality of the partitions, and wherein the step of detecting light includes a step of detecting light from a plurality of the partitions.

62. The method of paragraph 60 or 61, wherein the step of forming partitions includes a step of fusing droplets.

63. The method of any of paragraphs 60 to 62, wherein the step of forming partitions includes a step of forming droplets.

64. The method of any of paragraphs 60 to 63, wherein the reaction mixture is a dispersed phase of an emulsion.

65. A method of performing an assay, the method comprising: (A) forming a reaction mixture including a template for a target, a probe including a photoluminophore, and a sink that binds the probe to reduce an ability of the photoluminophore to emit light; (B) amplifying the target in the reaction mixture, at least in part by extending the probe; (C) detecting light that is dependent at least in part on a presence of the photoluminophore in the reaction mixture; and (D) determining a level of the target based on the light detected.

66. The method of paragraph 65, wherein the step of amplifying generates an amplicon and is performed with a first primer and a second primer that define respective ends of the amplicon, wherein the probe is the first primer, and wherein the second primer is conjugated to a quencher for the photoluminophore.

67. The method of paragraph 65 or 66, wherein the sink includes a quencher for the photoluminophore.

68. A composition, comprising: (A) a template; (B) a probe having a photoluminophore; and (C) a sink that is complementary to and binds the probe to reduce an ability of the photoluminophore to emit light.

69. The composition of paragraph 68, further comprising one or more primers to amplify a target from the template.

70. The composition of paragraph 68, wherein the probe is a primer for amplification of a target.

71. The composition of any of paragraphs 68 to 70, further comprising a polymerase.

72. The composition of paragraph 71, wherein the polymerase is heat stable.

73. The composition of any of paragraphs 68 to 72, further comprising a ligase.

74. The composition of any of paragraphs 68 to 73, further comprising dNTPs, NTPs, or both.

75. The composition of any of paragraphs 68 to 74, wherein the probe includes a quencher for the photoluminophore.

76. The composition of paragraph 75, wherein the quencher is a first quencher, and wherein the sink includes a second quencher for the photoluminophore.

77. The composition of any of paragraphs 68 to 76, wherein the template, the probe, and the sink are disposed in partitions, further comprising a same liquid continuous phase surrounding each of the partitions.

Example 17. Selected Embodiments II

This example describes selected embodiments of assay methods and compositions, presented as a series of indexed paragraphs.

1. A method of analysis, the method comprising: (A) forming at least one volume containing a reporter including a first oligomer and a second oligomer capable of base-pairing with one another below a melting temperature of the reporter to affect a photoluminescence detectable from the reporter; (B) amplifying a target in the at least one volume, at least in part by extending one or more primers at a temperature above the melting temperature of the reporter; (C) detecting the photoluminescence of the reporter from the at least one volume, optionally while the at least one volume is at a temperature below the melting temperature of the reporter; and (D) determining a property of the target based on the photoluminescence detected.

2. The method of paragraph 1, wherein the step of amplifying uses the first oligomer as a primer.

3. The method of paragraph 2 or paragraph 3, wherein the first oligomer includes a photoluminophore from which the photoluminescence is detected.

4. The method of any of paragraphs 1 to 3, wherein the first oligomer is fully complementary to the target.

5. The method of any of paragraphs 1 to 4, wherein the second oligomer includes a photoluminophore from which the photoluminescence is detected, and wherein the first oligomer includes an energy transfer partner of the photoluminophore.

6. The method of paragraph 5, wherein the energy transfer partner is a quencher.

7. The method of any of paragraphs 1 to 6, wherein the first oligomer has a longer chain of base-containing units than the second oligomer.

8. The method of any of paragraphs 1 to 7, wherein the first oligomer forms a hybrid with the target having a higher melting temperature than the melting temperature of the reporter.

9. The method of paragraph 8, wherein the higher melting temperature is at least ten degrees higher than the melting temperature of the reporter.

10. The method of any of paragraphs 1 to 4 and 7 to 9, wherein the first oligomer includes a photoluminophore from which the photoluminescence is detected and also includes an energy transfer partner of the photoluminophore, and wherein the second oligomer does not include an energy transfer partner of the photoluminophore.

11. The method of any of paragraphs 1 to 10, wherein the photoluminescence of the reporter decreases when the first oligomer and the second oligomer base-pair with one another.

12. The method of any of paragraphs 1 to 4 and 7 to 11, wherein the first oligomer includes a photoluminophore from which the photoluminescence is detected, and wherein an energy transfer partner of the photoluminophore is included in the second oligomer.

13. The method of paragraph 12, wherein the energy transfer partner is a quencher.

14. The method of paragraph 12 or 13, wherein an energy transfer partner of the photoluminophore also is included in the first oligomer.

15. The method of any of paragraphs 1 to 14, wherein the property is a level of the target.

16. The method of any of paragraphs 1 to 15, wherein the step of amplifying causes cleavage of the first oligomer, the second oligomer, or both the first oligomer and the second oligomer, and wherein the cleavage affects the photoluminescence detected.

17. The method of any of paragraphs 1 to 16, wherein the step of forming at least one volume includes a step of forming a plurality of partitions that contain the target at partial occupancy.

18. The method of paragraph 17, wherein the step of amplifying includes a step of exposing the plurality of partitions to a plurality of thermal cycles, and wherein the partitions are maintained continuously above the melting temperature of the reporter throughout the plurality of thermal cycles.

19. The method of any of paragraphs 1 to 3 and 5 to 18, wherein the first oligomer has (a) a region dedicated to base-pairing with the target such that the first oligomer functions as a primer included in the one or more primers and (b) another region dedicated to base-pairing with the second oligomer and not the target.

20. The method of any of paragraphs 1 to 19, wherein the first oligomer or the second oligomer includes a chain of base-containing units, and wherein a photoluminophore is attached to a 5'-end of the chain.

21. The method of any of paragraphs 1 to 4 and 7 to 20, wherein the first oligomer includes a photoluminophore from which the photoluminescence is detected, and wherein the second oligomer is fully complementary to the target.

22. The method of any of paragraphs 1 to 21, wherein the melting temperature of the reporter is less than about 45 degrees Celsius.

23. The method of any of paragraphs 1 to 4 and 6 to 22, wherein the first oligomer includes a photoluminophore, wherein the second oligomer includes a chain of base-containing units, and wherein the second oligomer includes an energy transfer partner of the photoluminophore.

24. The method of paragraph 23, wherein the energy transfer partner is attached to a 3'-end of the chain.

25. The method of paragraph 23, wherein the energy transfer partner is attached to a nonterminal unit of the chain.

26. The method of paragraph 23, wherein the energy transfer partner is attached to a 5'-end of the chain.

27. The method of any of paragraphs 1 to 26, wherein the second oligomer has one or more mismatches with the first oligomer when the first and second oligomers base-pair with one another.

28. The method of any of paragraphs 1 to 27, wherein each of the first oligomer and the second oligomer is at least partially complementary to the target.

29. The method of paragraph 28, wherein the second oligomer has one or more mismatches with the target.

30. The method of any of paragraphs 1 to 29, wherein a 3'-end of the first oligomer is aligned with a 5'-end of the second oligomer when the oligomers base-pair with one another.

31. The method of any of paragraphs 1 to 30, wherein a 5'-end of the first oligomer is aligned with a 3'-end of the second oligomer when the oligomers base-pair with one another.

32. The method of any of paragraphs 1 to 29 and 31, wherein a 3'-end of the first oligomer is aligned with an interior base-containing unit of the second oligomer when the oligomers base-pair with one another.

33. The method of any of paragraphs 1 to 30 and 32, wherein a 5'-end of the first oligomer is aligned with an interior base-containing unit of the second oligomer when the oligomers base-pair with one another.

34. The method of any of paragraphs 1 to 30, 32, and 33, wherein a 3'-end of the second oligomer is aligned with an interior base-containing unit of the first oligomer when the oligomers base-pair with one another.

35. The method of any of paragraphs 1 to 29 and 31 to 34, wherein a 5'-end of the second oligomer is aligned with an interior base-containing unit of the first oligomer when the oligomers base-pair with one another.

36. The method of any of paragraphs 1 to 35, the reporter being a first reporter, further comprising a second reporter including a pair of oligomers capable of base-pairing with one another below a melting temperature of the second reporter to affect a photoluminescence detectable from the second reporter and optionally distinguishable from the photoluminescence detectable from the first reporter, wherein the step of amplifying a target includes a step of extending a forward primer provided at least in part by one of the reporters and a step of extending a reverse primer provided at least in part by the other reporter, and wherein the property of the target is determined based on photoluminescence detected from each of the first and second reporters.

37. The method of paragraph 1, wherein the first oligomer includes a photoluminophore from which the photoluminescence is detected and also includes an energy transfer partner (and/or other modifier of the photoluminescence) of the photoluminophore.

38. The method of paragraph 37, wherein the energy transfer partner is a quencher.

39. The method of paragraph 37 or 38, wherein the photoluminescence of the reporter increases when the first oligomer and the second oligomer base pair with each other.

40. The method of any of paragraphs 37 to 39, wherein the step of amplifying a target uses the second oligomer as a primer.

41. The method of any of paragraphs 37 to 40, wherein the second oligomer does not include an energy transfer partner of the photoluminophore.

42. The method of any of paragraphs 37 to 41, wherein the step of amplifying a target does not degrade, or optionally at least stoichiometrically degrade, the first oligomer.

43. The method of any of paragraphs 37 to 42, wherein the step of amplifying a target increases the number of first oligomers that are not bound to second oligomers.

44. The method of any of paragraphs 37 to 43, wherein the first oligomer has a shorter chain of base-containing units than the second oligomer.

45. The method of any of paragraphs 37 to 44, wherein the first oligomer includes at least one of a second photoluminophore and a second energy transfer partner of the photoluminophore.

46. The method of any of paragraphs 37 to 45, wherein the step of detecting the photoluminescence of the reporter is performed while the at least one volume is at a temperature below the melting temperature of the reporter.

47. The method of any of paragraphs 37 to 46, wherein the property is a level of the target.

48. The method of any of paragraphs 37 to 47, wherein the step of forming at least one volume includes a step of forming a plurality of partitions that contain the target at partial occupancy.

49. The method of paragraph 48, wherein the partitions are droplets.

50. The method of paragraph 48 or 49, wherein the step of amplifying includes a step of exposing the plurality of partitions to a plurality of thermal cycles, and wherein the partitions are maintained continuously above the melting temperature of the reporter throughout the plurality of thermal cycles.

51. The method of any of paragraphs 37 to 50, the reporter being a first reporter, further comprising a second reporter including a pair of oligomers capable of base-pairing with one another below a melting temperature of the second reporter to affect a photoluminescence detectable from the second reporter and optionally distinguishable from the photoluminescence detectable from the first reporter, wherein the step of amplifying a target includes a step of extending a forward primer provided at least in part by one of the reporters and a step of extending a reverse primer provided at least in part by the other reporter, and wherein the property of the target is determined based on photoluminescence detected from each of the first and second reporters.

52. The method of any of paragraphs 37 to 51, further comprising one or more limitations of paragraphs 2 to 36 not inconsistent with the limitations of paragraphs 37 to 51, including but not limited to limitations describing the placement of photoluminophore(s) and energy transfer partner(s) of the photoluminophore(s), the details of amplification and detection, the relative alignment of the first oligomer and second oligomer, the presence of mismatches among the first and second oligomers and the target, and so on.

53. A method of analysis, the method comprising: (A) forming partitions each containing a reporter including a first oligomer having a photoluminophore and also including a second oligomer capable of base-pairing with the first oligomer below a melting temperature of the reporter to decrease, by energy transfer, a photoluminescence detectable from the photoluminophore; (B) exposing the partitions to a plurality of thermal cycles, to amplify a target sequence at least in part by extending one or more primers at a temperature above the melting temperature of the reporter, wherein the target sequence is present in only a subset of the partitions; (C) detecting the photoluminescence of the photoluminophore for each partition of a plurality of the partitions while the partition is at a temperature below the melting temperature of the reporter; and (D) determining a property of the target based on the photoluminescence detected.

54. The method of paragraph 53, wherein the partitions are maintained continuously above the melting temperature of the reporter throughout the plurality of thermal cycles.

55. The method of paragraph 53 or paragraph 54, wherein the first oligomer is a primer included in the one or more primers.

56. The method of any of paragraphs 53 to 55, wherein the photoluminophore is included in the first oligomer.

57. The method of any of paragraphs 53 to 56, wherein a quencher for the photoluminophore is included in the second oligomer.

58. The method of any of paragraphs 53 to 57, wherein a quencher for the photoluminophore is included in the first oligomer.

59. A composition, comprising: a plurality of partitions containing a target at partial occupancy and amplification reagents to amplify the target and also containing a reporter to detect target amplification, the reporter including a first oligomer having a photoluminophore and a second oligomer that is base-paired with the first oligomer to affect a photoluminescence detectable from the photoluminophore.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of analysis, the method comprising:
forming a mixture including a target;
forming a plurality of fluid volumes each containing a portion of the mixture, a reporter, and a pair of primers, wherein only a subset of the plurality of fluid volumes contain at least one copy of the target, the reporter including a first oligomer having a photoluminophore and a second oligomer having a quencher for the photoluminophore, the first oligomer and the second oligomer being capable of base-pairing with one another below the melting temperature of the reporter in the plurality of fluid volumes to quench photoluminescence of the photoluminophore, wherein the first oligomer and the second oligomer are not covalently linked to one another;
amplifying the target in the plurality of fluid volumes to produce an amplicon by extending the pair of primers at a temperature above the melting temperature of the reporter, wherein amplifying causes cleavage of the second oligomer, and wherein the cleavage increases the photoluminescence detectable from the photoluminophore of the first oligomer;
detecting photoluminescence from the photoluminophore contained by each fluid volume of the plurality of fluid volumes while the fluid volume is at a temperature below the melting temperature of the reporter, wherein fluid volumes of the plurality of fluid volumes that are positive for the target have more photoluminescence from the photoluminophore than fluid volumes of the plurality of fluid volumes that are negative for the target; and
determining a level of the target based on the photoluminescence detected.

2. The method of claim 1, wherein the mixture includes the reporter.

3. The method of claim 1, wherein the mixture includes the pair of primers.

4. The method of claim 1, wherein the plurality of fluid volumes are droplets, and wherein the droplets are enclosed by an immiscible liquid to create an emulsion.

5. The method of claim 1, wherein determining a level includes determining a number of the plurality of fluid volumes that contain the target or that do not contain the target based on the photoluminescence detected.

6. The method of claim 5, wherein the level is a concentration of the target.

7. The method of claim 1, wherein the second oligomer forms a hybrid with the target having a higher melting temperature than the melting temperature of the reporter.

8. The method of claim 1, wherein amplifying includes exposing the plurality of fluid volumes to a plurality of thermal cycles, and the plurality of fluid volumes are maintained continuously above the melting temperature of the reporter throughout each thermal cycle of the plurality of thermal cycles.

9. The method of claim 1, wherein each of the first and second oligomers has a chain of nucleotides, and wherein the chain of nucleotides of the second oligomer is longer than the chain of nucleotides of the first oligomer.

* * * * *

SEQUENCE LISTING

<160> NUMBER OF SEQ ID NOS: 13

<210> SEQ ID NO 1
<211> LENGTH: 19
<212> TYPE: DNA
<213> ORGANISM: Artificial sequence
<220> FEATURE:
<223> OTHER INFORMATION: CCND1 probe and primer
<220> FEATURE:
<221> NAME/KEY: FAM
<222> LOCATION: (1)..(1)
<223> OTHER INFORMATION: carboxyfluorescein label conjugated to first
      residue

<400> SEQUENCE: 1
tatctgaggg gcgggagag                                                    19

<210> SEQ ID NO 2
<211> LENGTH: 20
<212> TYPE: DNA
<213> ORGANISM: Artificial sequence
<220> FEATURE:
<223> OTHER INFORMATION: reverse primer

<400> SEQUENCE: 2
gaggtcacga cattttagcg                                                   20

<210> SEQ ID NO 3
<211> LENGTH: 13
<212> TYPE: DNA
<213> ORGANISM: Artificial sequence

```
<220> FEATURE:
<223> OTHER INFORMATION: sink
<220> FEATURE:
<221> NAME/KEY: IB
<222> LOCATION: (13)..(13)
<223> OTHER INFORMATION: Iowa Black(R) dark quencher conjugated to last
      residue

<400> SEQUENCE: 3
cgccsctcag ata                                                          13

<210> SEQ ID NO 4
<211> LENGTH: 21
<212> TYPE: DNA
<213> ORGANISM: Artificial sequence
<220> FEATURE:
<223> OTHER INFORMATION: forward primer for CCND1

<400> SEQUENCE: 4
acattgattc agcctgtttg g                                                 21

<210> SEQ ID NO 5
<211> LENGTH: 21
<212> TYPE: DNA
<213> ORGANISM: Artificial sequence
<220> FEATURE:
<223> OTHER INFORMATION: reverse primer for CCND1

<400> SEQUENCE: 5
gaattcatcg gaaccgaact t                                                 21

<210> SEQ ID NO 6
<211> LENGTH: 22
<212> TYPE: DNA
<213> ORGANISM: Artificial sequence
<220> FEATURE:
<223> OTHER INFORMATION: probe for CCND1
<220> FEATURE:
<221> NAME/KEY: FAM
<222> LOCATION: (1)..(1)
<223> OTHER INFORMATION: carboxyfluorescein label conjugated to first
      residue
<220> FEATURE:
<221> NAME/KEY: IB
<222> LOCATION: (22)..(22)
<223> OTHER INFORMATION: Iowa Black(R) dark quencher conjugated to last
      residue

<400> SEQUENCE: 6
tccttgcacc catgcctgtc ca                                                22

<210> SEQ ID NO 7
<211> LENGTH: 20
<212> TYPE: DNA
<213> ORGANISM: Artificial sequence
<220> FEATURE:
<223> OTHER INFORMATION: foward primer for K-Ras

<400> SEQUENCE: 7
agaagcaatg ccctctcaag                                                   20

<210> SEQ ID NO 8
<211> LENGTH: 20
<212> TYPE: DNA
<213> ORGANISM: Artificial sequence
<220> FEATURE:
<223> OTHER INFORMATION: reverse primer for K-Ras

<400> SEQUENCE: 8
```
aaacaggctc aggacttagc                                             20

<210> SEQ ID NO 9
<211> LENGTH: 26
<212> TYPE: DNA
<213> ORGANISM: Artificial sequence
<220> FEATURE:
<223> OTHER INFORMATION: K-Ras probe
<220> FEATURE:
<221> NAME/KEY: HEX
<222> LOCATION: (1)..(1)
<223> OTHER INFORMATION: hexachloro-fluorescein label conjugated to
      first residue
<220> FEATURE:
<221> NAME/KEY: IB
<222> LOCATION: (26)..(26)
<223> OTHER INFORMATION: Iowa Black(R) dark quencher conjugated to last
      residue

<400> SEQUENCE: 9
attgaaacat cagcaaagac aagaca                                      26

<210> SEQ ID NO 10
<211> LENGTH: 27
<212> TYPE: DNA
<213> ORGANISM: Artificial sequence
<220> FEATURE:
<223> OTHER INFORMATION: K-Ras probe
<220> FEATURE:
<221> NAME/KEY: FAM
<222> LOCATION: (1)..(1)
<223> OTHER INFORMATION: carboxyfluorescein label conjugated to first
      residue
<220> FEATURE:
<221> NAME/KEY: IB
<222> LOCATION: (27)..(27)
<223> OTHER INFORMATION: Iowa Black(R) dark quencher conjugated to last
      residue

<400> SEQUENCE: 10
ttgaaacatc aacaaagaca agacagg                                     27

<210> SEQ ID NO 11
<211> LENGTH: 13
<212> TYPE: DNA
<213> ORGANISM: Artificial sequence
<220> FEATURE:
<223> OTHER INFORMATION: sink
<220> FEATURE:
<221> NAME/KEY: IB
<222> LOCATION: (13)..(13)
<223> OTHER INFORMATION: Iowa Black(R) dark quencher conjugated to last
      residue

<400> SEQUENCE: 11
gttgatgttt caa                                                    13

<210> SEQ ID NO 12
<211> LENGTH: 26
<212> TYPE: DNA
<213> ORGANISM: Artificial sequence
<220> FEATURE:
<223> OTHER INFORMATION: K-Ras probe
<220> FEATURE:
<221> NAME/KEY: HEX
<222> LOCATION: (1)..(1)
<223> OTHER INFORMATION: hexachloro-fluorescein label conjugated to
      first residue

<400> SEQUENCE: 12
attgaaacat cagcaaagac aagaca 26

<210> SEQ ID NO 13
<211> LENGTH: 27
<212> TYPE: DNA
<213> ORGANISM: Artificial sequence
<220> FEATURE:
<223> OTHER INFORMATION: K-Ras probe
<220> FEATURE:
<221> NAME/KEY: FAM
<222> LOCATION: (1)..(1)
<223> OTHER INFORMATION: carboxyfluorescein label conjugated to first
      residue

<400> SEQUENCE: 13
ttgaaacatc aacaaagaca agacagg 27